United States Patent
Hattori et al.

(10) Patent No.: US 10,190,895 B2
(45) Date of Patent: Jan. 29, 2019

(54) METHOD FOR ASSEMBLING GAS SENSOR, AND GAS SENSOR ASSEMBLY APPARATUS

(71) Applicant: NGK INSULATORS, LTD., Nagoya-shi, Aichi (JP)

(72) Inventors: Tetsuya Hattori, Konan (JP); Hiroyuki Tanaka, Nagoya (JP); Kenji Kato, Handa (JP); Shigeki Takeshita, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 340 days.

(21) Appl. No.: 15/069,996

(22) Filed: Mar. 15, 2016

(65) Prior Publication Data
US 2016/0273944 A1    Sep. 22, 2016

(30) Foreign Application Priority Data

Mar. 16, 2015   (JP) .................................. 2015-052146
Mar. 4, 2016    (JP) .................................. 2016-042050

(51) Int. Cl.
    *G01D 11/30*    (2006.01)
    *G01N 27/407*    (2006.01)

(52) U.S. Cl.
CPC ......... *G01D 11/30* (2013.01); *G01N 27/4078* (2013.01)

(58) Field of Classification Search
CPC ........... G01N 27/4071; G01N 27/4078; G01N 33/0009; G01M 15/02
See application file for complete search history.

(56) References Cited

U.S. PATENT DOCUMENTS

| 4,591,423 A | 5/1986 | Kato et al. |
| 4,802,369 A * | 2/1989 | Morii ................. G01N 27/4077 204/424 |

(Continued)

FOREIGN PATENT DOCUMENTS

| JP | 6-226557 A | 8/1994 |
| JP | 06226557 A * | 8/1994 |

(Continued)

OTHER PUBLICATIONS

Translation of JP 06226557 A (provided by applicant).*
The Extended European Search Report for the corresponding European patent application No. 16160709.8 dated Oct. 19, 2016.

*Primary Examiner* — Lisa Caputo
*Assistant Examiner* — Nathaniel T Woodward
(74) *Attorney, Agent, or Firm* — Global IP Counselors, LLP

(57) ABSTRACT

A method for assembling a gas sensor includes fitting through holes of annular mounting parts with an element dummy disposed vertically and whose cross-sectional shape perpendicular is similar to that of a sensor element. The annular mounting parts are a plurality of parts including a ceramic powder compact. A tubular body is fitted with outer peripheries of the annular mounting parts, and then, the element is abuttingly disposed on an upper end of the dummy. Subsequently, the dummy is moved vertically downward to fit the through holes of the annular mounting parts with the element, thereby obtaining a workpiece. The workpiece is vertically inverted, and with the element tip being in contact with a sealing assist jig that has a buffer performance, the upper end of the uppermost annular mounting part is pressed vertically downward to compress the powder compact, thereby sealing an inside of the tubular body.

32 Claims, 15 Drawing Sheets

(56) References Cited

U.S. PATENT DOCUMENTS

| | | | | |
|---|---|---|---|---|
| 6,546,783 | B2* | 4/2003 | Shirai | C03C 8/24 |
| | | | | 204/424 |
| 6,550,309 | B1* | 4/2003 | Noda | G01N 27/407 |
| | | | | 204/424 |
| 9,851,334 | B2* | 12/2017 | Isaka | G01N 33/0009 |
| 2003/0015020 | A1* | 1/2003 | Geier | G01N 27/4077 |
| | | | | 73/23.31 |
| 2008/0116068 | A1* | 5/2008 | Matsuo | G01N 27/4077 |
| | | | | 204/400 |
| 2014/0102170 | A1 | 4/2014 | Kato | |

FOREIGN PATENT DOCUMENTS

| | | |
|---|---|---|
| JP | 2005-37372 A | 2/2005 |
| WO | 2013/005491 A1 | 1/2013 |

\* cited by examiner

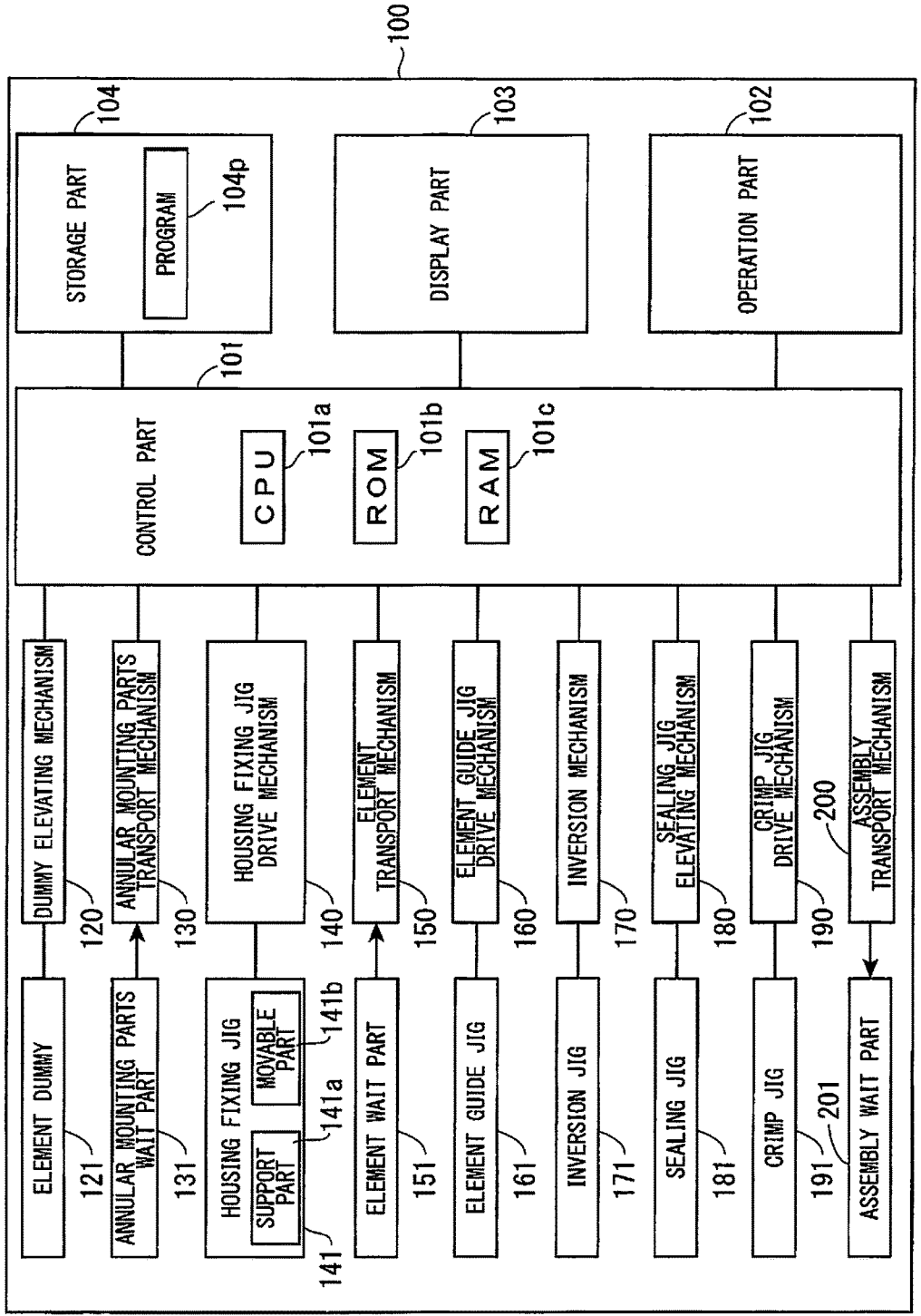
F I G. 4

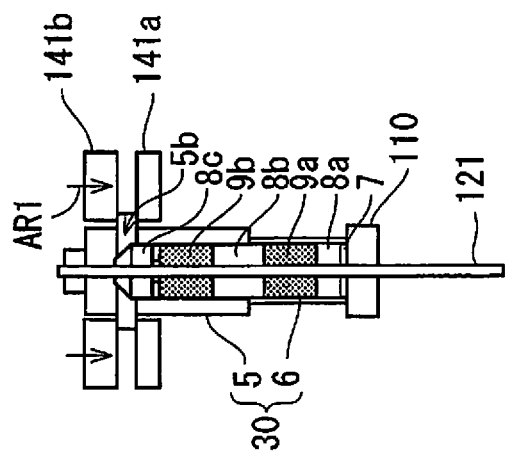
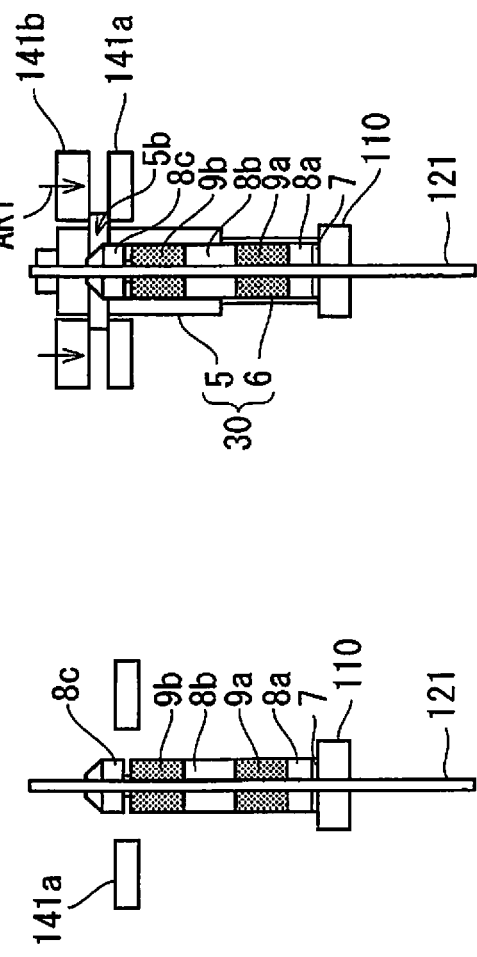
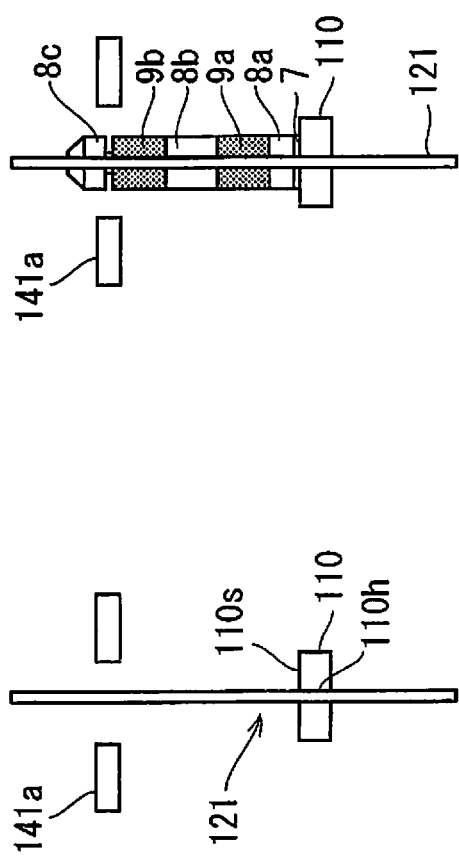

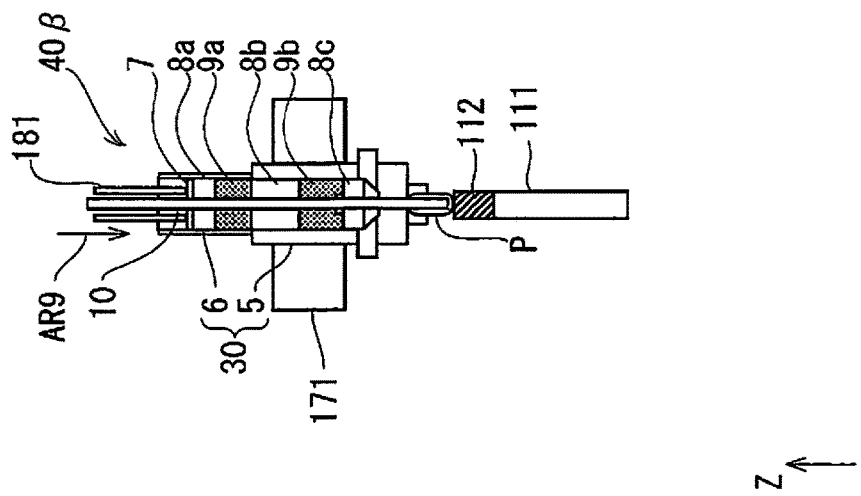
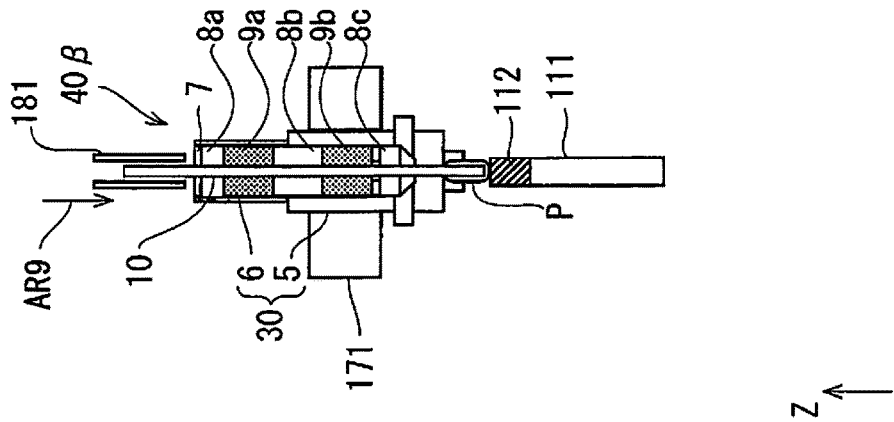

F I G. 15A
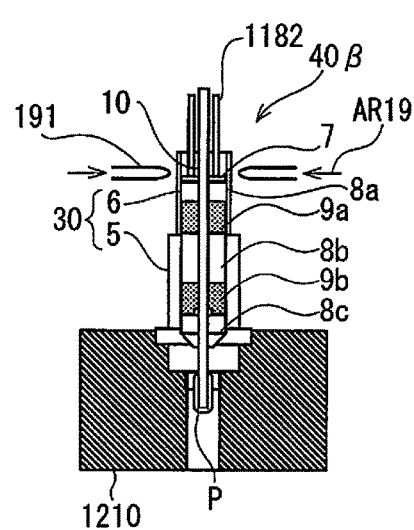
F I G. 15B
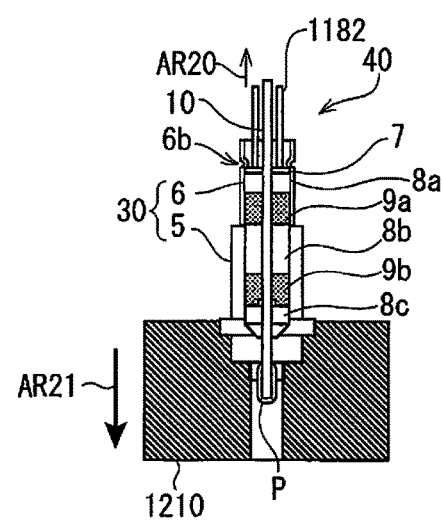

METHOD FOR ASSEMBLING GAS SENSOR, AND GAS SENSOR ASSEMBLY APPARATUS

BACKGROUND OF THE INVENTION

Field of the Invention

The present invention relates to a method for assembling a gas sensor including a ceramic sensor element and to an assembly apparatus for use in assembling the same.

Description of the Background Art

A gas sensor including a sensor element formed of oxygen-ion conductive solid electrolyte ceramic such as zirconia ($ZrO_2$) has been conventionally known as a device that measures the concentration of a predetermined gas component of a measurement gas such as an exhaust gas and a combustion gas in an internal combustion engine, usually a car engine.

In such a gas sensor, an elongated-plate-shaped ceramic sensor element (detection element) is usually fixed by a plurality of ceramic supporters which are ceramic insulators glass and by ceramic powder compacts each filled between the ceramic supporters, such as talc, and is hermetically sealed with the powder compacts in a metal housing and a hollow portion of a cylindrical inner tube welded and fixed to the housing. The method and apparatus for preferably assembling such a gas sensor have been known (for example, see WO 2013/005491 and Japanese Patent Application Laid-Open No. 2005-37372).

In the technique disclosed in WO 2013/005491, even when a sensor element warps and a dimensional tolerance between the sensor element and a plurality of members (annular mount members, annular mounting parts) to be annularly mounted is small, the annular mount members (annular mounting parts) can be annularly mounted with reliability.

In the technique disclosed in WO 2013/005491, the annular mount members are annularly mounted to the sensor element from an end at the side at which the opening for introducing a measurement gas into the element is provided. Thus, the application of this technique to a sensor element, whose surface at the side of the relevant end is covered with a protective film (protective layer), is not preferred because the protective film may be damaged or peeled off.

Japanese Patent Application Laid-Open No. 2005-37372 discloses a method for manufacturing a gas sensor including a detection element whose one end side is covered with a protective layer. In the method disclosed in Japanese Patent Application Laid-Open No. 2005-37372, however, a plurality of annular mounting parts are once annularly mounted to a pin member similar in shape to the detection element, the pin member is pulled out so that the plurality of annular mounting parts are stacked, and then the detection element is inserted into the stacked annular mounting parts. Consequently, the annular mounting parts are likely to slide out of place when the pin member is pulled out or the detection element is inserted.

SUMMARY OF THE INVENTION

The present invention is directed to a method for assembling a gas sensor including a ceramic sensor element and an assembly apparatus for use in assembling the same.

A method for assembling a gas sensor according to the present invention includes the steps of: (a) disposing an element dummy with its longitudinal direction coinciding a vertical direction, the element dummy having a shape similar to a shape of a sensor element including ceramic as a main constituent material and having an elongated shape; (b) fitting through holes of annular mounting parts with the element dummy from vertically above, the annular mounting parts each having a disc shape or cylindrical shape, the through holes each having a shape corresponding to a cross-sectional shape of the sensor element; (c) fitting a tubular body with outer peripheries of the annular mounting parts from vertically above; (d) abuttingly disposing the sensor element on an upper end of the element dummy such that the element dummy and the sensor element are arranged in line with each other; (e) moving the element dummy vertically downward to move down the sensor element and fitting the through holes of the annular mounting parts with the sensor element, to thereby obtain a workpiece including the sensor element, the annular mounting parts, and the tubular body; (f) vertically inverting a posture of the workpiece; and (g) pressing the annular mounting parts. In the step (a), a plurality of types of parts including a powder compact of ceramic are fitted with the element dummy as the annular mounting parts. The step (g) includes a step of compressing the powder compact and is performed at least after the step (f).

According to the present invention, the annular mounting parts are always annularly mounted to the element dummy or the sensor element in the assembly of the gas sensor, thus preferably preventing an occurrence of a problem in which the sensor element cannot be assembled due to an occurrence of a positional deviation. Additionally, breakage of the element tip is preferably prevented when the inside of the gas sensor is sealed with a powder compact.

Preferably, in the step (g), with the tip of the sensor element, which is located as a lowermost end of the workpiece after the step (f), being in contact with the sealing assist jig, the part located at an uppermost position among the annular mounting parts is pressed vertically downward, so that the powder compact is compressed to seal the inside of the tubular body. The sealing assist jig has a buffer performance against an impact exerted from vertically above.

In another aspect of the present invention, the step (g) includes (g-1) a step of compressing the powder compact of the workpiece being in a first posture, and (g-2) a step of compressing the powder compact of the workpiece being in a second posture. The first posture is a posture of the workpiece before being vertically inverted in the step (f). The second posture is a posture of the workpiece after being vertically inverted in the step (f). Letting an upper end and a lower end of the sensor element when the workpiece is in the first posture be respectively a first tip and a second tip: in the step (g-1), while the sensor element is positioned from below the second tip with a predetermined positioning jig, a first force is applied to the annular mounting parts vertically upward to compress the powder compact; in the step (f), the workpiece in which the powder compact has been compressed in the step (g-1) is vertically inverted; and in the step (g-2), while the workpiece vertically inverted in the step (f) is supported from below and simultaneously the first tip of the sensor element located at a lowermost end of the workpiece is prevented from abutting another member, a second force greater than the first force is applied to the annular mounting parts vertically downward to further compress the powder compact, to thereby seal an inside of the tubular body.

According to the aspect, a gas sensor is assembled with a low risk of chipping or cracking occurring in the sensor element compared with a manner of performing sealing only once.

The present invention therefore has an object to provide a method for assembling a gas sensor capable of preferably assembling a gas sensor.

BRIEF DESCRIPTION OF THE DRAWINGS

FIG. 4 is a block diagram showing a schematic configuration of an assembly apparatus 100;

FIGS. 5A, 5B, and 5C are schematic cross-sectional views of an assembly 40 according to a first embodiment during assembly;

FIGS. 8A and 8B are schematic cross-sectional views of the assembly 40 according to the first embodiment during assembly;

FIGS. 15A and 15B are schematic cross-sectional views of the assembly 40 according to the second embodiment during assembly.

DESCRIPTION OF THE PREFERRED EMBODIMENTS

First Embodiment
Configuration of Gas Sensor

Figure 1:
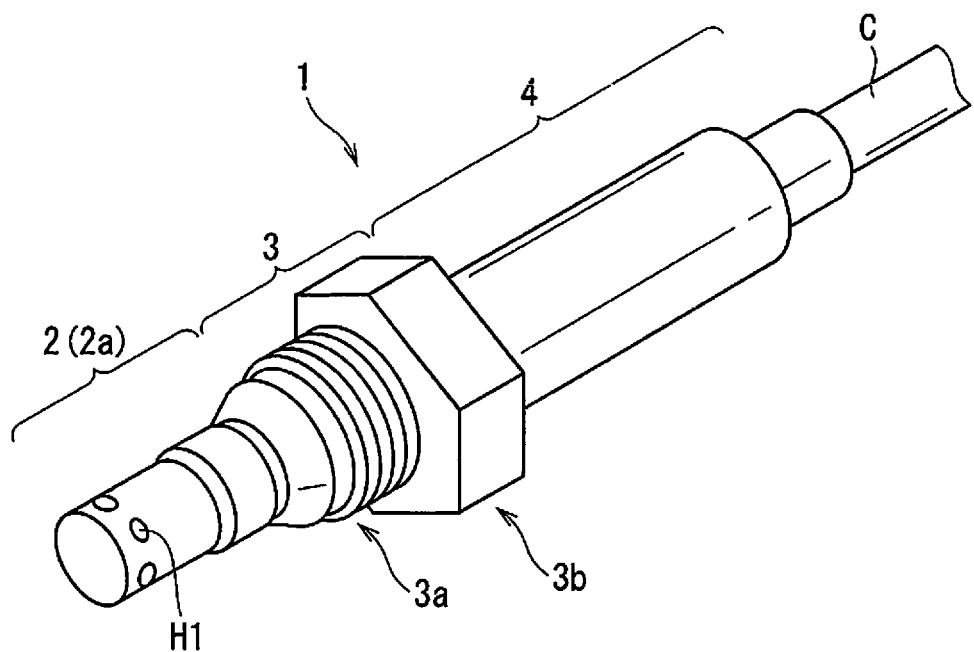
FIG. 1 is an external perspective view of a gas sensor (more specifically, a main body thereof) to be assembled in embodiments.
Figure 2:
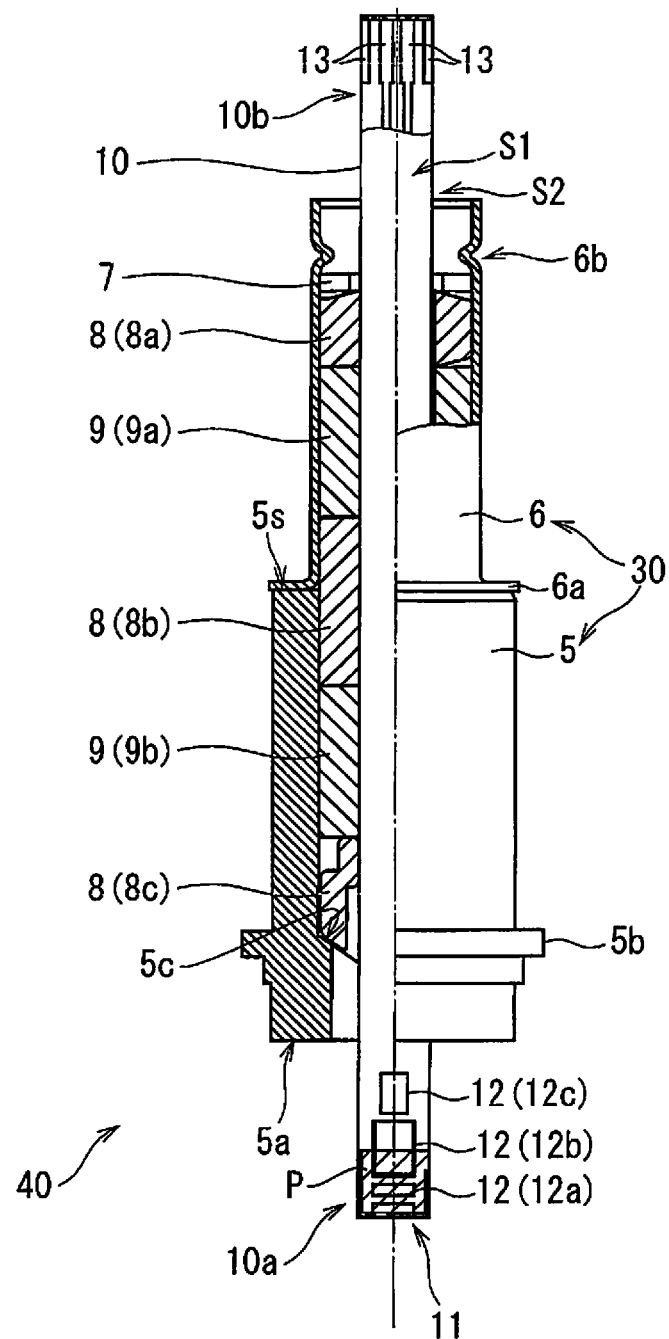
FIG. 2 is a partial cross-sectional view of main components inside the gas sensor 1.

FIG. 1 is an external perspective view of a gas sensor (more specifically, a main body thereof) 1 to be assembled in a first embodiment. FIG. 2 is a partial cross-sectional view of main components inside the gas sensor 1. In this embodiment, the gas sensor 1 serves to detect a predetermined gas component (e.g., NOx) by a sensor element 10 (FIG. 2) inside the gas sensor 1.

The sensor element 10 is an elongated columnar or thin-plate-shaped member including, as a main constituent material, an element body of oxygen-ion conductive solid electrolyte ceramic such as zirconia. The sensor element 10 has a configuration in which a gas inlet, an internal space, and the like are provided at a side of a first tip 10a, and various electrodes and a wiring pattern are provided on the surface and inside of the element body. In the sensor element 10, a detection gas introduced into the internal space is reduced or decomposed in the internal space, to thereby generate oxygen ions. The gas sensor 1 determines the concentration of the gas component based on a fact that an amount of oxygen ions flowing through the element is proportional to the concentration of the gas component in a detection gas. With reference to FIG. 2, the surface coinciding the front is referred to as a main surface S1 of the sensor element 10, and the surface that is perpendicular to the main surface S1 and extends longitudinally is referred to as a lateral surface S2. The surface of the sensor element 10 within a predetermined range from the first tip 10a in the longitudinal direction of the sensor element 10 is covered with a protective film P (see FIG. 2). The protective film P is a porous film provided to protect the first tip 10a and its vicinity from thermal shock, which is made of, for example, $Al_2O_3$ and has a thickness of approximately 10 to 2000 μm, and is also referred to as a thermal-shock-resistant protective film. In light of its objective, the protective film P should preferably be formed so as to resist forces up to approximately 50 N. The formation range of the protective film P in FIG. 2 and the following drawings is merely an example, and actually, the formation range is appropriately determined in accordance with a specific structure of the sensor element 10.

The exterior of the gas sensor 1 is mainly composed of a first cover 2, a fixing bolt 3, and a second cover 4.

The first cover 2 is an approximately cylindrical exterior member that protects a portion of the sensor element 10 which directly comes into contact with the detection gas at the time of use, which is specifically the first tip 10a including a gas inlet 11 and closed spaces 12 (buffer space 12a, first internal space 12b, second internal space 12c). For easy understanding, FIG. 2 and the following drawings show that the gas inlet 11 and the closed spaces 12 (buffer space 12a, first internal space 12b, second internal space 12c) are formed on the main surface S. In actuality, however, these parts are not exposed on the main surface S1 but are each provided inside the sensor element 10 except for the gas inlet 11 being open at the first tip 10a that is the lowermost end of the sensor element 10 in FIG. 2.

More specifically, the first cover 2 has a double-layer structure of an outside cover 2a and an inside cover (not shown). Each of the outside cover 2a and the inside cover has a cylindrical shape and is closed at one side, and has a plurality of through holes in its lateral portion, through which a gas passes. FIG. 1 illustrates through holes H1 provided in the outside cover 2a, which are merely an example. The position and the number of through holes disposed can be appropriately determined in consideration of how a measurement gas flows into the first cover 2.

The fixing bolt 3 is an annular member to be used when the gas sensor 1 is fixed at a measurement position. The fixing bolt 3 includes a threaded bolt portion 3a and a holding portion 3b to be held when the bolt portion 3a is screwed. The bolt portion 3a is screwed with a nut provided at a position at which the gas sensor 1 is mounted. For example, the bolt portion 3a is screwed with a nut portion provided in the car exhaust pipe, which causes the gas sensor 1 to be fixed to the exhaust pipe in such a manner that the first cover 2 side of the gas sensor 1 is exposed in the exhaust pipe.

The second cover 4 is a cylindrical member that protects other parts of the gas sensor 1. From the end of the second cover 4, a cable C for electrically connecting the gas sensor 1 and a drive control part (not shown) extends.

FIG. 2 shows the internal configuration of the gas sensor 1, more specifically, the configuration of the gas sensor 1 except for the first cover 2, the fixing bolt 3, and the second cover 4 shown in FIG. 1.

As shown in FIG. 2, inside the gas sensor 1, a washer 7, three ceramic supporters 8 (8a, 8b, 8c), and two powder compacts 9 (9a, 9b) are each annularly mounted to the portion of the sensor element 10 except for the first tip 10a, which includes the gas inlet 11 and the like, and a second tip 10b, which includes terminals 13 for connection with the cable C, in such a manner that the sensor element 10 is positioned about their axes. The ceramic supporters 8 are made of ceramic insulator. The powder compacts 9 are obtained by shaping ceramic powders such as talc. In the following description, the washer 7, the ceramic supporters 8, and the powder compacts 9 may be collectively referred to as annular mounting parts.

Figure 3:
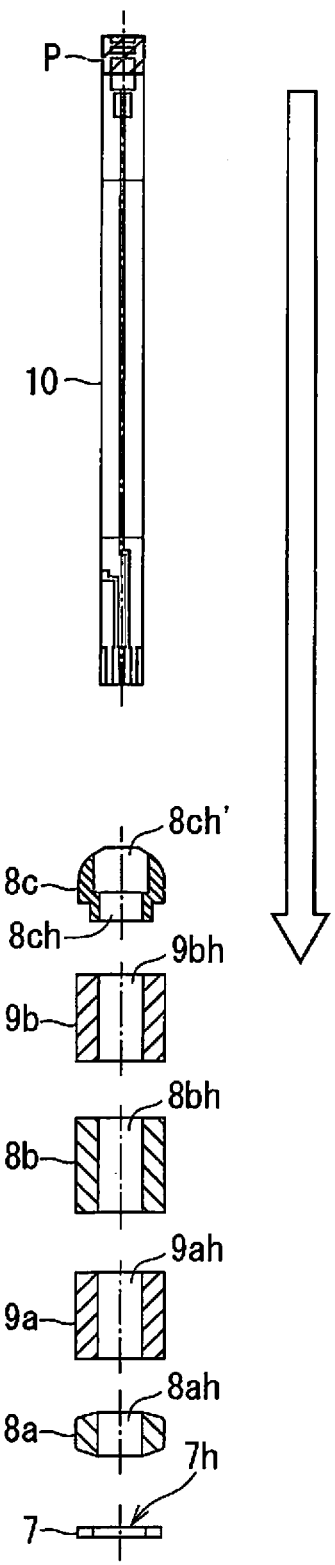
FIG. 3 schematically shows how a washer 7, ceramic supporters 8, and powder compacts 9 are annularly mounted to a sensor element 10.

FIG. 3 schematically shows how the washer 7, the ceramic supporters 8 (8a, 8b, 8c), and the powder compacts 9 (9a, 9b) are annularly mounted to the sensor element 10.

As shown in FIG. 3, such annular mounting is enabled by inserting the end (second tip 10b) of the sensor element 10 at the side, at which the protective film P is not provided, into the ceramic supporter 8c, the powder compact 9b, the ceramic supporter 8b, the powder compact 9a, the ceramic supporter 8a, and the washer 7 in the stated order. The respective members have a circular plate shape or cylindrical shape. For such annular mounting, a through hole 7h of cylindrical shape is provided at the center axis of the washer 7, and through holes 8ah, 9ah, 8bh, 9bh, and 8ch of rectangular shape corresponding to the cross-sectional shape of the sensor element 10 are respectively provided in the ceramic supporter 8a, the powder compact 9a, the ceramic supporter 8b, the powder compact 9b, and the ceramic supporter 8c. These through holes are fitted with the sensor element 10, thereby causing the respective members to be annularly mounted to the sensor element 10. The portion of the ceramic supporter 8c opposite the through hole 8ch is an opening 8ch' larger than the through hole 8ch. The washer 7, the ceramic supporters 8, and the powder compacts 9 are disposed coaxially with one another.

From the viewpoint of attaining airtightness, the through holes of the ceramic supporters 8 and the through holes of the powder compacts 9 are configured such that a difference with the design cross-sectional size of the sensor element 10 is 0.25 to 0.35 mm and a dimensional tolerance is 0.1 mm. The through hole 7h of the washer 7 is provided such that a difference with the design cross-sectional size of the sensor element 10 is at least 1 mm or more and 1.3 mm or less. The washer 7, the ceramic supporters 8, and the powder compacts 9 are configured so as to have a difference of no more than approximately 0.35 mm in outside diameter value.

As shown in FIG. 2, a cylindrical tubular body (inner tube welded product) 30 including a housing 5 being a ceramic cylindrical member and an inner tube 6 being a metal cylindrical member, which are integrated with each other, is annularly mounted to the outer peripheries of the washer 7, the ceramic supporters 8 (8a, 8b, 8c), and the powder compacts 9 (9a, 9b). In the following description, the body having the configuration in which the tubular body 30 is annularly mounted is referred to as an assembly 40.

The tubular body 30 is formed integrally by welding a bend 6a bent outwardly, which is included at one end of the inner tube 6, to an end surface 5s of the housing 5. The housing 5 and the inner tube 6 have substantially the same inside diameter and are connected coaxially. The inside diameter of the tubular body 30 is set to be greater than a design value of the maximum outside diameter of each annular mounting part.

At one side inside the housing 5, a tapered portion 5c is provided. At the position of the inner tube 6 immediately above the washer 7, a recess 6b recessed inwardly is formed. The tapered portion 5c and the recess 6b cause the washer 7, the ceramic supporters 8 (8a, 8b, 8c), and the powder compacts 9 (9a, 9b) that are annularly mounted to the sensor element 10 to be locked inside the tubular body 30.

More specifically, the powder compacts 9 are compressed after being annularly mounted, and are accordingly in intimate contact with the sensor element 10. The recess 6b is provided after the powder compacts 9 are compressed. With the intimate contact achieved between the powder compacts 9 and the sensor element 10, the sensor element 10 is fixed inside the tubular body 30, and a space between the first tip 10a side of the sensor element 10, which includes the gas inlet 11, and the second tip 10b, which includes the terminals 13 for connection with the cable C, is sealed. This achieves airtightness between a measurement gas space, which is in contact with the first tip 10a of the sensor element 10 and in which a detection gas (measurement gas) is present, and a reference gas space, which is in contact with the second tip 10b and in which a reference gas such as air is present. The recess 6b is provided to keep the compressed states of the powder compacts 9.

The resultant product obtained by coating the assembly product 40 having the above configuration with the first cover 2, the fixing bolt 3, and the second cover 4 is the gas sensor 1. Specifically, the first cover 2 is connected to a tubular portion 5a at the tip of the housing 5. The fixing bolt 3 is annularly mounted to the outer periphery of the housing 5 so as to come into contact with a projection portion (flanged portion) 5b. Moreover, the second cover 4 is mounted so as to be fitted into an annular groove between the fixing bolt 3 and the housing 5, which is formed by the annular mounting above.

The above-mentioned configuration allows the gas sensor 1 to completely cut off the atmosphere (the atmosphere in the first cover 2) around the first tip 10a of the sensor element 10 from the outside atmosphere while being mounted at a predetermined position. This enables accurate measurement of the concentration of a target gas component in a detection gas.

Procedure for Assembling Assembly

The procedure for assembling the assembly 40 performed in this embodiment will now be described. FIG. 4 is a block diagram showing a schematic configuration of the assembly apparatus 100 that performs the assembly above.

The assembly apparatus 100 includes a control part 101, an operation part 102, a display part 103, and a storage part 104. The control part 101 is mainly composed of a CPU 101a, a ROM 101b, and a RAM 101c and controls the overall operation of the assembly apparatus 100. The operation part 102 is an input interface composed of switches, buttons, a touch panel, and the like for providing various execution instructions to the assembly apparatus 100. The display part 103 includes a display for displaying various operation menus and the operation state of the assembly apparatus 100 and instruments. The storage part 104 mainly stores an operation program 104p and operational condition data (not shown) of the assembly apparatus 100. The assembly apparatus 100 automatically processes a series of assembly operations described below by the control part 101 executing the operation program 104p.

The assembly apparatus 100 further includes, as components that actually execute the assembly operations, a dummy elevating mechanism 120 performing an operation of moving up and down the element dummy 121, an annular mounting parts transport mechanism 130 transporting annular mounting parts from an annular mounting parts wait part 131 to a predetermined position, a housing fixing jig drive mechanism 140 performing an operation of movement a housing fixing jig 141, an element transport mechanism 150 transporting a sensor element 10 from an element wait part 151 to a predetermined position, an element guide jig drive mechanism 160 performing an operation of movement an element guide jig 161, an inversion mechanism 170 performing an operation of inverting a workpiece 40β (described below) with an inversion jig 171, a sealing jig elevating mechanism 180 performing an operation of moving up and down a sealing jig 181, a crimp jig drive mechanism 190 performing an operation of movement a crimp jig 191, and an assembly transport mechanism 200 transporting a complete assembly 40 to an assembly wait part 201.

FIGS. 5A, 5B, 5C, 6A, 6B, 6C, 7, 8A, 8B, 9A, and 9B are schematic cross-sectional views of the assembly 40 during assembly for explaining the procedure in assembling the assembly 40 by the assembly apparatus 100. In FIGS. 5A to 9B, the vertically upward direction is represented by the z-axis direction.

As shown in FIG. 5A, first, the element dummy 121 is inserted through a support 110.

The support 110 is a member for supporting the annular mounting parts from below in the step of assembling the assembly 40. The support 110 has a flat horizontal surface 110s at the vertical upper side and has a through hole 110h through which the element dummy 121 is inserted.

The element dummy 121 is a member whose cross-section perpendicular to its longitudinal direction has a shape similar to the longitudinal cross-sectional shape of the sensor element 10 and which has an elongated plate shape similarly to the sensor element 10. The element dummy 121 is movable up and down vertically by the dummy elevating mechanism 120 not shown in FIGS. 5A, 5B, and 5C. The element dummy 121, however, does not need to be made of ceramic similarly to the sensor element 10 and may be formed of an appropriate material in consideration of durability, wear resistance, or the like. The element dummy 121 has a thickness and a width somewhat greater than those of the sensor element 10 though it is smaller than the through holes of the ceramic supporters 8 and the powder compacts 9. The element dummy 121 is inserted into the support 110 from the vertical lower side of the support 110 by the dummy elevating mechanism 120 and is disposed with its longitudinal direction coinciding the vertical direction. In this case, the dummy elevating mechanism 120 functions as dummy disposing means for disposing the element dummy 121 with its longitudinal direction coinciding the vertical direction. In such a case, the element dummy 121 is inserted up to a position at which the distance between the vertical upper portion of the element dummy 121 and the horizontal surface 110s of the support 110 is greater than a total of the thicknesses of all the annular mounting parts.

After the insertion of the element dummy 121 completes, subsequently, the annular mounting parts are annularly mounted to the element dummy 121, and then, the tubular body 30 is annularly mounted.

First, the annular mounting parts transport mechanism 130 not shown in FIGS. 5A, 5B, and 5C transports the annular mounting parts, which have been transported from the outside of the apparatus in advance and caused to wait at the annular mounting parts wait part 131, to the element dummy 121 in the order of the washer 7, the ceramic supporter 8a, the powder compact 9a, the ceramic supporter 8b, the powder compact 9b, and the ceramic supporter 8c, and fits the through holes of the respective parts with the element dummy 121. This results in a state in which, as shown in FIG. 5B, the respective annular mounting parts sequentially fitted with the element dummy 121 are supported by the upper end of the support 110 from vertically below. In this case, the annular mounting parts transport mechanism 130 functions as annular mounting part fitting means for fitting the through holes of the annular mounting parts with the element dummy 121.

When the annular mounting completes, subsequently, the annular mounting parts transport mechanism 130 transports the tubular body 30, which has been transported from the outside of the apparatus and caused to wait at the annular mounting parts wait part 131 as described above, to above the element dummy 121 with the annular mounting parts annularly mounted thereto, and further, moves down the tubular body 30 with the inner tube 6 pointing vertically downward to fit the tubular body 30 with the outer peripheries of the annular mounting parts. This results in a state in which, as shown in FIG. 5C, the annular mounting parts fitted with the tubular body 30 are supported by the upper end of the support 110 from vertically below. In this case, the annular mounting parts transport mechanism 130 functions as tubular body fitting means for fitting the tubular body 30 with the outer peripheries of the annular mounting parts.

More specifically, the annular mounting parts transport mechanism 130 moves down the tubular body 30 until a projection portion 5b of the housing 5 abuts a support part 141a that constitutes the housing fixing jig 141 from above. This abutment allows the tubular body 30 to be supported by the support part 141a from vertically below. In other words, the vertical height level of the tubular body 30 is defined by the support part 141a. After the projection portion 5b is supported by the support part 141a from vertically below in the above state, the housing fixing jig drive mechanism 140 not shown in FIG. 5 moves down a movable part 141b of the housing fixing jig 141, which has retracted to a predetermined retraction position (not shown), toward the projection portion 5b from vertically above as indicated by the arrow AR1 and causes the movable part 141b to abut the projection portion 5b. As shown in FIG. 5C, consequently, the housing fixing jig 141 grips and fixes the projection portion 5b of the housing 5. In other words, the tubular body 30 including the housing 5 is fixed by the housing fixing jig 141.

The transport of the washer 7, the ceramic supporters 8, and the powder compacts 9, fitting of these annular mounting parts with the element dummy 121, and fitting of the tubular body 30 with the outer peripheries of these annular mounting parts by the annular mounting parts transport mechanism 130 may be performed by an annular mounting parts transport mechanism 130 including transport arms whose constructions and materials correspond to the shapes and materials of the respective parts, using these transport arms.

The support part 141a and the movable part 141b constituting the housing fixing jig 141 may have any shape in which the projection portion 5b of the housing 5 can be gripped and fixed from vertically above. For example, the support part 141a and the movable part 141b may be formed of a pair of members of symmetrical shape or may be formed of one member of C-shape or U-shape in plan view. The support part 141a and the movable part 141b may have different shapes.

Figure 6A:
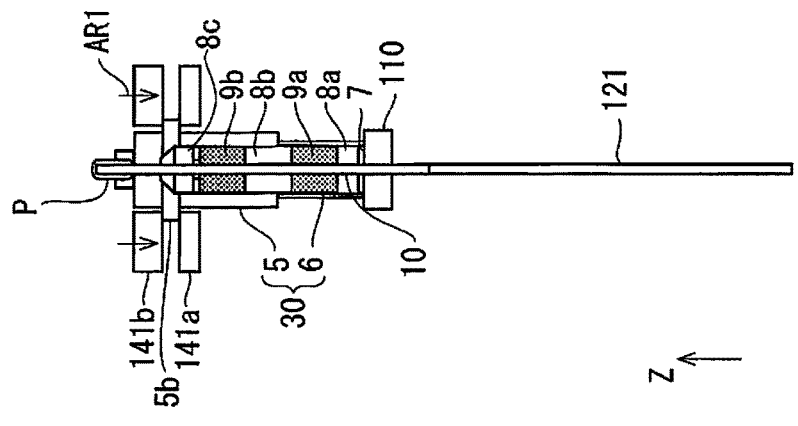
FIGS. 6A, 6B, and 6C are schematic cross-sectional views of the assembly 40 according to the first embodiment during assembly.
Figure 6B:
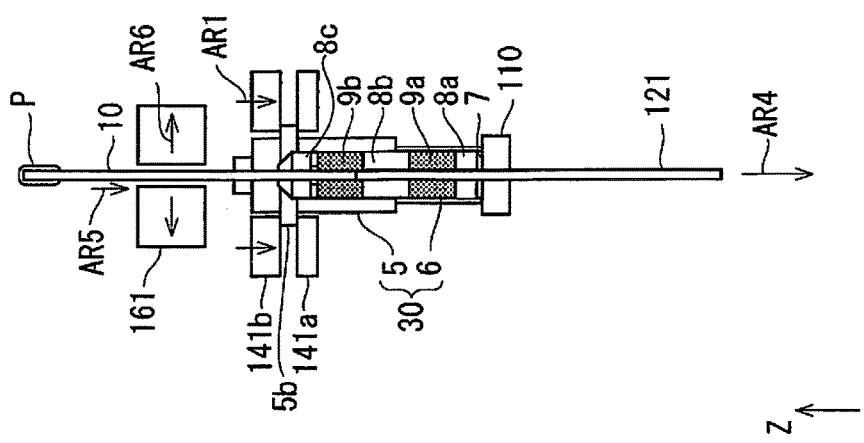
Figure 6C:
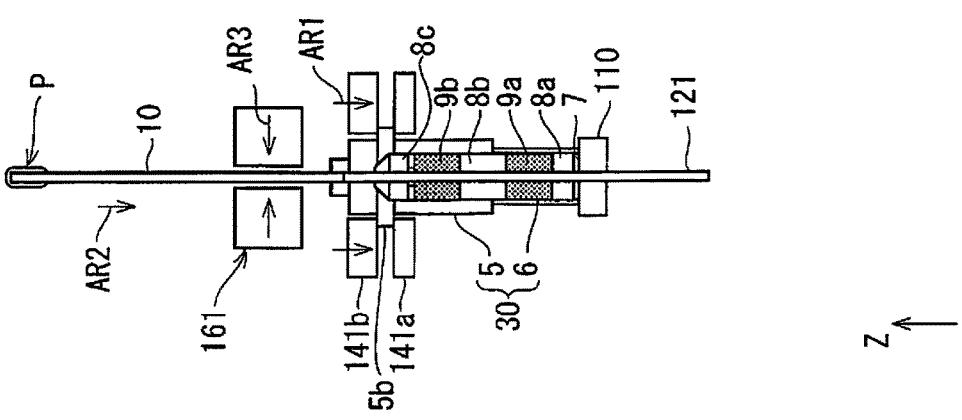

When the tubular body 30 including the housing 5 is fixed as described above, subsequently, as shown in FIG. 6A, the sensor element 10 is abuttingly disposed to the element dummy 121 so as to be arranged in line with the element dummy 121, with the sensor element 10 being in a posture in which its tip (first tip 10a) at the side at which the protective film P is formed is located at the upper side. This position of the sensor element 10 is implemented by the movement of the element transport mechanism 150 not shown in FIGS. 6A, 6B, and 6C of transporting the sensor element 10, which has been transported from the outside of the apparatus in advance and caused to wait at the element wait part 151, to above the element dummy 121 so as not to come into contact with the protective film P and further of moving down the sensor element 10 vertically above the element dummy 121 and causing the sensor element 10 to abut the upper end of the element dummy 121, as indicated by the arrow AR2 in FIG. 6A. The element transport mechanism 150 holds the sensor element 10 at this position. In this case, the element transport mechanism 150 functions as element disposing means for abuttingly disposing the sensor element 10 on the upper end of the element dummy 121. In FIGS. 6A, 6B, and 6C and the following drawings, the thickness of the protective film P is exaggerated. The thickness of the protective film P is actually designed to such an extent that does not affect the annular mounting of the annular mounting parts and the tubular body 30 described below.

A specific configuration of the element transport mechanism 150 may be any configuration in which the sensor element 10 can be preferably transported and held so as not to come into contact with the protective film P.

When the sensor element 10 is disposed as described above, the element guide jig drive mechanism 160 not shown in FIGS. 6A, 6B, and 6C runs, so that the element guide jig 161 is disposed at the position lateral to the sensor element 10, as indicated by the arrow AR3 in FIG. 6A. The element guide jig 161 is disposed to support and guide the sensor element 10 when the sensor element 10 is moved vertically downward. The surface of the element guide jig 161, which faces the sensor element 10, is thus formed of a material that does not damage the sensor element 10 if the sensor element 10 comes into contact with the surface, and is disposed so as to extend vertically at a position at which the surface comes closer to or comes into contact with the sensor element 10.

When the element guide jig 161 is disposed, holding of the sensor element 10 by the element transport mechanism 150 is released, so that the sensor element 10 enters the state in which the lower end (second tip 10b) thereof is supported by the element dummy 121. In addition, the dummy elevating mechanism 120 not shown in FIGS. 6A, 6B, and 6C runs again, so that as indicated by the arrow AR4 in FIG. 6B, the element dummy 121 is moved vertically downward. Correspondingly to the element dummy 121 moving downward, the sensor element 10 whose lower end (second tip 10b) has been supported by the element dummy 121 also moves vertically downward. In the through holes of the annular mounting parts, accordingly, the sensor element 10 gradually replaces the element dummy 121, resulting in a state in which the annular mounting parts are annularly mounted to the sensor element 10. In this case, the dummy elevating mechanism 121 functions as element fitting means for fitting the through holes of the annular mounting parts with the sensor element 10.

The annular mounting parts are always annularly mounted to the element dummy 121 or the sensor element 10 in the manner above, which preferably restricts an occurrence of a problem in which annular mounting parts have a positional deviation and the sensor element 10 accordingly cannot be incorporated.

As the sensor element 10 moves downward to some extent so that the sensor element 10 begins to move vertically downward without being supported and guided by the element guide jig 161, the element guide jig drive mechanism 160 runs again to separate the element guide jig 161 from the sensor element 10, as indicated by the arrow AR6 in FIG. 6B. This is also for preventing the protective film P from coming into contact with the element guide jig 161.

The sensor element 10 is moved down by moving down the element dummy 121 until, as shown in FIG. 6C, the sensor element 10 penetrates through the washer 7 and the upper end (first tip 10a) of the sensor element 10 reaches the position of the upper end of the housing 5. Although a specific degree to which the upper end of the sensor element 10 projects from the housing 5 can be appropriately determined, as described below, the sensor element 10 is positioned at a predetermined position before the assembly 40 is eventually obtained.

After the completion of the sensor element 10 moving downward, the inversion mechanism 170 not shown in FIG. 7 vertically inverts the posture of the assembly 40 during assembly which has undergone up to the insertion of the sensor element 10 (which is hereinafter referred to as a workpiece 40β).

Figure 7:
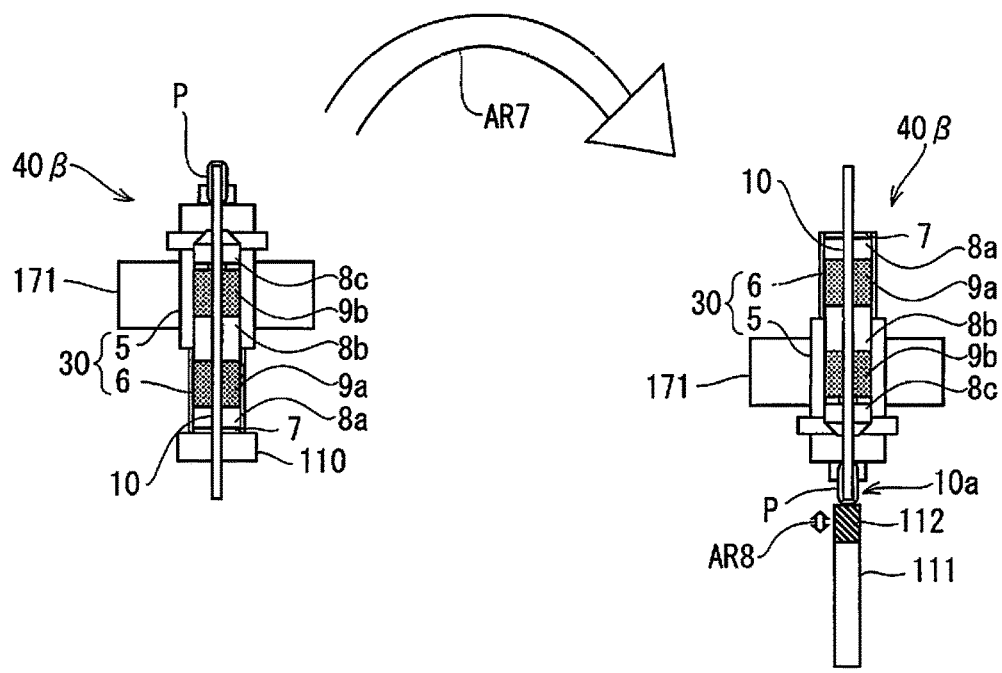
FIG. 7 is a schematic cross-sectional view of the assembly 40 according to the first embodiment during assembly.

Specifically, first, the inversion mechanism 170 drives the inversion jig 171 simultaneously with the release of the fixing by the housing fixing jig 141 (retraction of the housing fixing jig 141), and as shown in FIG. 7, the inversion jig 171 is caused to hold the workpiece 40β from the lateral side of the workpiece 40β. More specifically, the workpiece 40β is held from the lateral side of the housing 5.

Subsequently, as indicated by the arrow AR7, the inversion mechanism 170 rotates the inversion jig 171 holding the workpiece 40β by 180° together with the workpiece 40β. This vertically inverts the posture of the workpiece 40β. In this case, the inversion jig 171 and the inversion mechanism 170 function as inversion means for vertically inverting the posture of the workpiece 40β. Specific configurations of the inversion jig 171 and the inversion mechanism 170 may be any configuration in which the posture of the workpiece 40β can be inverted preferably.

Further, subsequent to the inversion of its posture, the inversion mechanism 170 moves the inversion jig 171 while holding the workpiece 40β, thereby disposing the workpiece 40β such that the first tip 10a of the sensor element 10 covered with the protective film P, which is positioned as the lowermost end after the inversion, comes into contact with the vertical upper end of a sealing assist jig 111.

The sealing assist jig 111 is a member for positioning the sensor element 10 (restricting a positional deviation of the sensor element 10) in sealing by compression of the powder compacts 9 (9a, 9b). The sealing assist jig 111 includes an impact buffer 112 formed of a material (cushion material) having a buffer performance (anti impact performance) against an impact (load) exerted from above, on the vertical upper end. Specifically, the impact buffer 112 is provided so as to deform (contract) vertically in accordance with the magnitude of the impact (load) to be exerted, as indicated by the arrow AR8 in FIG. 7, thereby mitigating the impact (load) exerted. The workpiece 40β whose posture has been inverted as described above is disposed in such a manner that the first tip 10a of the sensor element 10, which is covered with the protective film P, is in contact with the impact buffer 112.

The impact buffer 112 is formed of a material having Rockwell hardness (HRC) of 1 or more and 200 or less to have a thickness of approximately 0.1 mm or more and 1.0 mm or less in the vertical direction. By satisfying these values, the assembly apparatus 100 preferably mitigates impacts exerted on the protective film P and the sensor element 10 and preferably restricts the displacement of the sensor element 10 in sealing by the sealing jig 181 described below. As the material for the impact buffer 112, a resin material such as polypropylene is exemplified. The impact buffer 112 may be provided densely or may be provided as a porous body such as foam.

When the posture of the workpiece 40β is inverted and is disposed on the sealing assist jig 111 in the manner described above, subsequently, as shown in FIGS. 8A and 8B, the inside of the workpiece 40β is sealed by the compression of the powder compacts 9 (9a, 9b) using the sealing jig 181.

The sealing jig 181 is a cylindrical member with its longitudinal direction coinciding the vertical direction. The sealing jig 181 is movable up and down vertically by the sealing jig elevating mechanism 180 not shown in FIGS. 8A and 8B. The outside diameter of the sealing jig 181 which is perpendicular to its longitudinal direction is smaller than the outside diameters of the washer 7, the ceramic supporters 8, and the powder compacts 9, and the inside diameter of the sealing jig 181 is greater than the maximum sizes of the through holes of the washer 7, the ceramic supporters 8, and the powder compacts 9. This structure allows the sealing jig 181 to depress the annular mounting parts from the vertical upper ends thereof.

In sealing, first, the sealing jig elevating mechanism 180 disposes the sealing jig 181 at a position vertically above the workpiece 40β held by the inversion jig 171 at which the workpiece 40β is coaxial with the sealing jig 181. Subsequently, as indicated by the arrow AR9 in FIG. 8A, the sealing jig elevating mechanism 180 moves down the sealing jig 181. As the sealing jig 181 starts moving downward, the sealing jig 181 eventually abuts the upper surface of the washer 7, which is positioned at the uppermost position among the annular mounting parts annularly mounted to the sensor element 10. As the sealing jig 181 is moved down further from this state, as shown in FIG. 8B, the washer 7 and further the whole of the annular mounting parts are pressed vertically downward inside the tubular body 30 whose outer periphery is held by the inversion jig 171. In this case, the position of the tubular body 30 is fixed through the fixing by the inversion jig 171, and consequently, the powder compacts 9 (9a, 9b) are compressed to predetermined thicknesses between the washer 7 and the ceramic supporter 8c. As a result, a space between the first tip 10a side of the sensor element 10, which includes the gas inlet 11, and the second tip 10b, which includes the terminals 13 for connection with the cable C, is sealed. This achieves airtightness between the measurement gas space and the reference gas space in the gas sensor 1. In this case, the sealing jig 181 and the sealing jig elevating mechanism 180 function as press means for compressing the powder compact by pressing. If the sealing jig 181 preferably functions as such press means, the tip thereof that abuts the washer 7 does not need to be formed continuously in its radial direction and can be formed non-continuously, for example, can have a slit.

Although the sensor element 10 is also fixed inside the tubular body 30 through the sealing with the compression of the powder compacts 9 in the manner above, until the sensor element 10 is fixed as described above, the sensor element 10 is displaceable vertically though it is partially in contact with the annular mounting parts and the housing 5. In the assembly apparatus 100 according to this embodiment, however, by causing the first tip 10a of the sensor element 10 (more specifically, the protective film P) to come into contact with the sealing assist jig 111 prior to sealing as described above, the sensor element 10 can be prevented from sliding out of place vertically downward from its originally disposed position along with sealing, thus keeping the position of the sensor element 10 within a predetermined tolerance.

Besides, the impact buffer 112 is provided at the vertical upper end of the sealing assist jig 111, so that the force by which the sensor element 10 is pressed against the sealing assist jig 111 along with the pressing by the sealing jig 181 is absorbed by the impact buffer 112. This preferably prevents a situation in which an impact associated with pressing is exerted on the protective film P covering the first tip 10a or further the first tip 10a itself, and consequently, the protective film P and the first tip 10a are damaged.

The impact buffer 112 does not necessarily exhibit an operational advantage only when it is used to assemble the sensor element 10 with the protective film P. The impact buffer 112 has an effect of preventing damage to the first tip 10a including the gas inlet 11 and the vicinity of the first tip 10a in sealing even when the sensor element 10 without the protective film P is to be assembled.

Figure 9A:
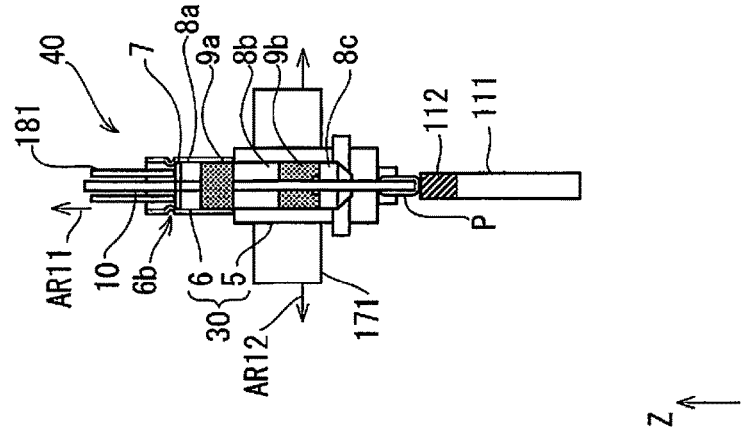
FIGS. 9A and 9B are schematic cross-sectional views of the assembly 40 according to the first embodiment during assembly.
Figure 9B:
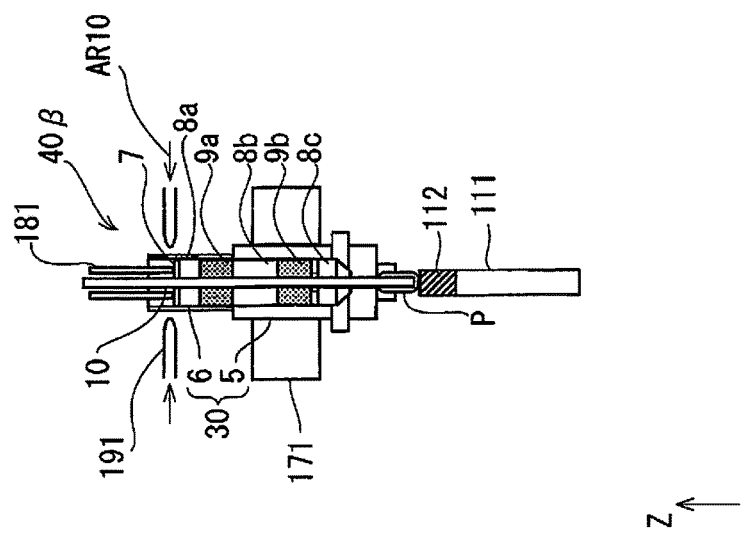

When the sealing jig 181 completes sealing, the crimp jig drive mechanism 190 crimps the inner tube 6. Specifically, with the sealing jig 181 performing pressing, the crimp jig drive mechanism 190 not shown in FIGS. 9A and 9B runs, thus causing, as indicated by the arrow AR10 in FIG. 9A, the crimp jig 191 to approach the inner tube 6 from the lateral side of the inner tube 6 and crimp the inner tube 6 from its outer peripheral side at the height level immediately above the washer 7. Since the compression of the powder compacts 9 by the sealing jig 181 described above provides a space that is located inside the inner tube 6 and is above the washer 7, as shown in FIG. 9B, such crimping preferably forms the recess 6b at the position immediately above the washer 7 in the inner tube 6. The formation of the recess 6b prevents the annular mounting parts from falling off in the following steps, and the annular mounting parts are locked inside the tubular body 30 as described above. In this case, the crimp jig 191 and the crimp jig drive mechanism 190 function as crimp means for forming the recess 6b that locks the annular mounting parts in the inner tube 6 constituting the tubular body 30. Subsequent to the formation of the recess 6b, retightening may be performed in which the inner tube 6 is crimped at the posture lateral to the powder compact 9a. This more reliably locks the annular mounting parts inside the tubular body 30 and provides hermitical sealing in the gas sensor 1.

The formation of the recess 6b (or retightening performed thereafter) described above completes the assembly 40. After the formation of the recess 6b, the sealing jig elevating mechanism 180 not shown in FIGS. 9A and 9B runs again, thus causing the sealing jig 181 to retract to a predetermined retraction position as indicated by the arrow AR11 in FIG. 9B. Finally, the assembly transport mechanism 200 not shown in FIGS. 9A and 9B transports the assembly 40 to the assembly wait part 201. A specific configuration of the assembly transport mechanism 200 may be any configuration that can preferably transport the assembly 40.

Consequently, the assembly procedure in the assembly apparatus 100 completes. When another assembly 40 is assembled subsequently, a similar procedure is repeated from the state shown in FIG. 5A. The resultant assembly 40 is taken out of the assembly apparatus 100 and is equipped with the first cover 2, the fixing bolt 3, and the second cover 4. This completes (the main body of) the gas sensor 1.

The annular mounting parts are always annularly mounted to the element dummy or the sensor element through the procedure for assembling an assembly performed in this embodiment. This state preferably prevents an occurrence of a problem in which a sensor element cannot be incorporated due to an occurrence of a positional deviation.

The first tip of the sensor element provided with an opening does not pass through the through holes of the annular mounting parts, and thus, even in the use of a sensor element including a protective film at the first tip side, assembling can be performed preferably.

Positioning of the sensor element by the sealing assist jig preferably prevents a positional deviation occurring in the sensor element when the assembly is sealed.

The sealing assist jig, which includes the impact buffer, prevents the protective film provided on the sensor element or the sensor element itself from experiencing a strong impact in sealing, thereby sealing the assembly without damaging the protective film or the sensor element.

Modification of First Embodiment

The assembly apparatus 100 according to the first embodiment is configured as follows: the impact buffer 112 provided at the vertical upper end of the sealing assist jig 111 provides a buffer performance against an impact exerted from vertically above to the sealing assist jig 111, and damage to the protective film P is prevented by performing sealing while causing the protective film P provided at the first tip 10a of the sensor element 10 to be in contact with the impact buffer 112. The configuration of the sealing assist jig 111, however, is not limited to the above and may be any configuration that can mitigate an impact exerted on the protective film P in pressing by the sealing jig 181.

Figure 10:
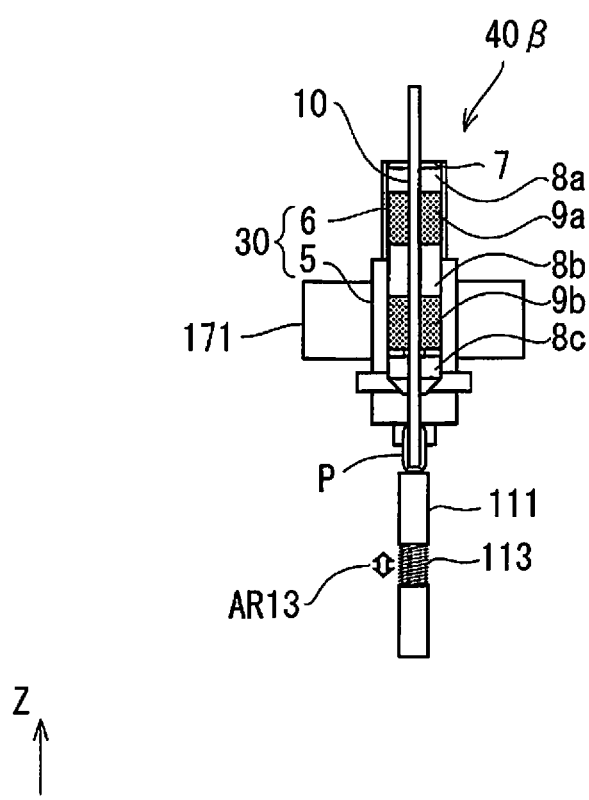
FIG. 10 is a schematic cross-sectional view of a modification of the first embodiment.

FIG. 10 schematically shows a sealing assist jig 111 having a configuration different from that of the first embodiment. The sealing assist jig 111 shown in FIG. 10 includes, in its vertical midway portion, an impact buffer 113 formed of an elastic member that is elastic in the vertical direction. A preferable example of the impact buffer 113 is formed of a spring member. Also when this sealing assist jig 111 is provided, as in the embodiment described above, the workpiece 40β is inverted by the inversion mechanism 170, and further, is disposed such that the first tip 10a of the sensor element 10 covered with the protective film P comes into contact with the vertical upper end of the sealing assist jig 111.

The sealing assist jig 111 is provided with the impact buffer 113 though its vertical upper end is merely a horizontal surface, and thus, also in the configuration shown in FIG. 10, the force by which the sensor element 10 is pressed against the sealing assist jig 111 is absorbed by the impact buffer 113 in pressing by the sealing jig 181. This preferably prevents a situation in which an impact associated with pressing is exerted on the protective film P covering the first tip 10a, and consequently, the protective film P and the first tip 10a are damaged.

Similarly to the impact buffer 112, the impact buffer 113 does not necessarily exhibit an operational advantage only when it is used to assemble the sensor element 10 provided with the protective film P. In other words, the impact buffer 113 has an effect of preventing damage to the first tip 10a provided with the gas inlet 11 and the vicinity of the first tip 10a even when the sensor element 10 not provided with the protective film P is to be assembled.

Second Embodiment

In the first embodiment and the modification thereof described above, the workpiece 40β is inverted vertically, and then, in sealing the inside of the tubular body 30, the jig that has a buffer performance against an impact exerted from vertically above is used as the sealing assist jig 111 supporting the sensor element 10 from below. This enables sealing without damage to the protective film P and the first tip 10a even when the first tip 10a of the sensor element 10 is provided with the protective film P. The manner of sealing the inside of the tubular body 30, however, is not limited to this. In this embodiment, sealing is performed separately in two stages during assembly of the assembly 40. This will now be described in detail.

Figure 11:
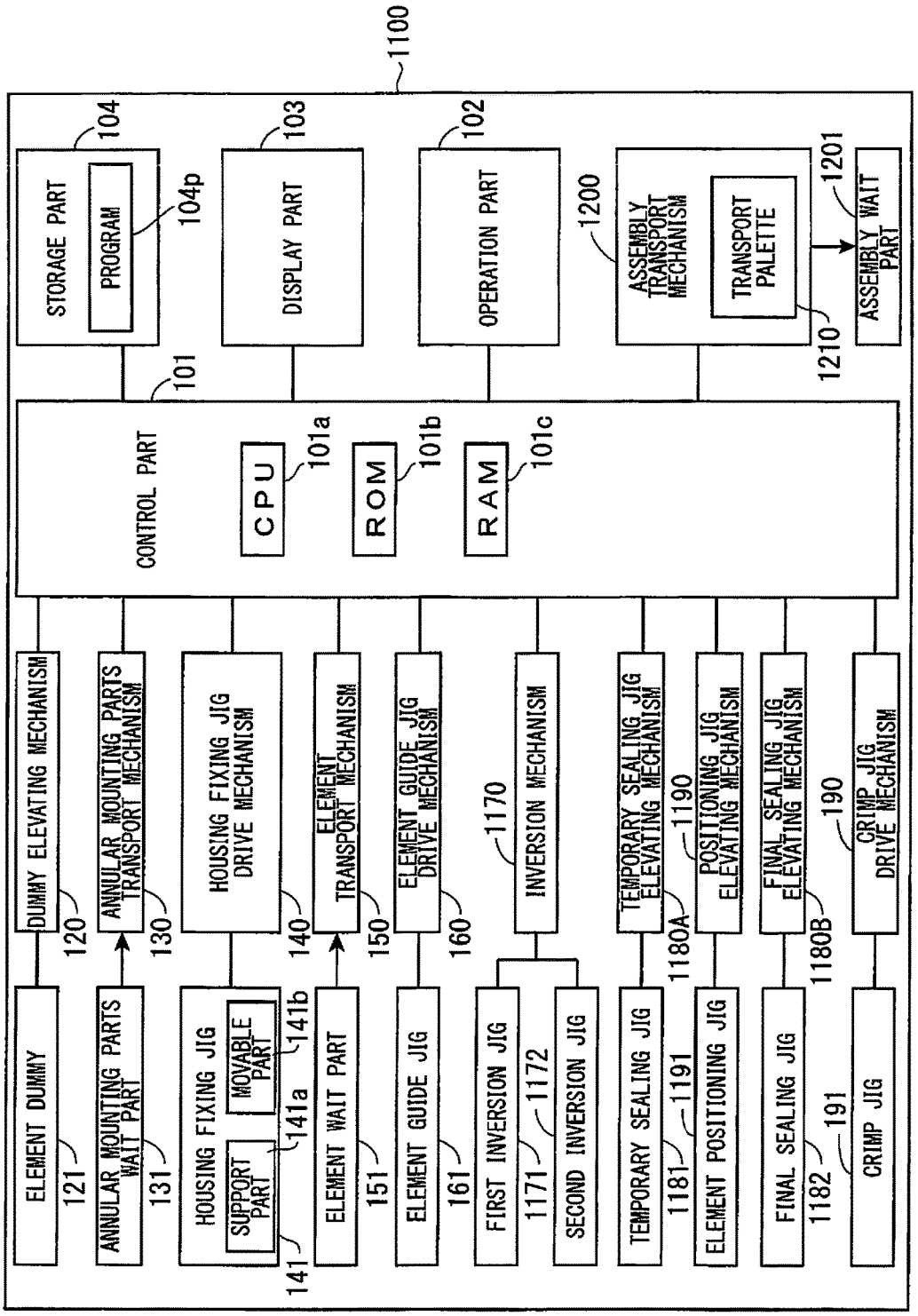
FIG. 11 is a block diagram showing a schematic configuration of an assembly apparatus 1100.

FIG. 11 is a block diagram showing a schematic configuration of an assembly apparatus 1100 that assembles an assembly 40 in this embodiment. Some of the components of the assembly apparatus 1100 are common with the components of the assembly apparatus 100 according to the first embodiment. These components are denoted by references similar to those of the assembly apparatus 100, and detailed description thereof will be omitted.

Specifically, the assembly apparatus 1100 includes, as components similar to those of the assembly apparatus 100, the control part 101 mainly composed of the CPU 101a, the ROM 101b, and the RAM 101c, the operation part 102, the display part 103, the storage part 104 storing the operation program 104p and the like, the dummy elevating mechanism 120, the element dummy 121, the annular mounting parts transport mechanism 130, the annular mounting parts wait part 131, the housing fixing jig drive mechanism 140, the housing fixing jig 141 including the support part 141a and the movable part 141b, the element transport mechanism 150, the element wait part 151, the element guide jig drive mechanism 160, the element guide jig 161, the crimp jig drive mechanism 190, and the crimp jig 191.

The assembly apparatus 1100 further includes, as components that actually perform assembly operations, an inversion mechanism 1170 performing an operation of inverting the workpiece 40β with the first inversion jig 1171 and the second inversion jig 1172, a temporary sealing jig elevating mechanism 1180A performing an operation of moving up and down a temporary sealing jig (depressing jig) 1181, a final sealing jig elevating mechanism 1180B performing an operation of moving up and down a final sealing jig (abutment jig) 1182, a positioning jig elevating mechanism 1190 performing an operation of moving up and down an element positioning jig 1191, an assembly transport mechanism 1200 transporting the workpiece 40β and the assembly 40, and an assembly wait part 1201 storing the assembled assembly 40.

FIGS. 12A, 12B, 13, 14A, 14B, 15A, and 15B are schematic cross-sectional views of the assembly 40 during assembly for explaining the procedure for assembling the assembly 40 by the assembly apparatus 1100. Also in FIGS. 12A to 15B, the vertically upward direction is represented by the z-axis direction as in FIGS. 5A to 9B.

Of the procedure for assembling the assembly 40 by the assembly apparatus 1100, annularly mounting of the annular mounting parts to the element dummy 121, annularly mounting of the tubular body 30 to the outer peripheries of the annular mounting parts, and changing of the element dummy 121 and the sensor element 10 are performed as in the first embodiment, that is, as in the manner shown in FIGS. 5A to 6C. Description thereof will thus be omitted in this embodiment.

Figure 12A:
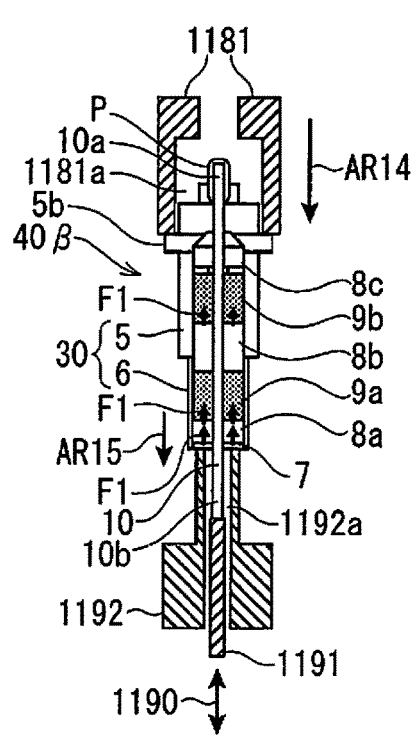
FIGS. 12A and 12B are schematic cross-sectional views of an assembly 40 according to a second embodiment during assembly.

After changing of the sensor element 10 and the element dummy 121 completes, the workpiece 40β is transported by the assembly transport mechanism 1200 while keeping its posture and, as shown in FIG. 12A, is placed on the sealing assist jig (support jig) 1192.

The sealing assist jig 1192 is a cylindrical member, included in the assembly apparatus 1100, with a flat upper end and its longitudinal direction coinciding the z-axis direction, and is configured to support the workpiece 40β from below by its upper end abutting the washer 7. The outside diameter of the upper end of the sealing assist jig 1192 is smaller than the inside diameter of the tubular body 30 (and the outer diameter of each annular mounting part). The inside diameter of the upper end of the sealing assist jig 1192 is greater than a maximum size of the through hole of each annular mounting part.

The second tip 10b of the sensor element 10 projecting vertically downward is inserted into the through hole 1192a of the sealing assist jig 1192 in the placing of the workpiece 40β (supporting the workpiece 40β from below). For this reason, the sealing assist jig 1192 does not interfere with the sensor element 10. Here, the element positioning jig 1191 is provided in the through hole 1192a.

The element positioning jig 1191 serves to determine the position at which the sensor element 10 is disposed vertically (to posture the sensor element 10) in temporary sealing described below. The element positioning jig 1191 is movable up and down vertically by the positioning jig elevating mechanism 1190 and is disposed such that its upper end is disposed at the position at which the lower end of the sensor element 10 is disposed after temporary sealing.

Although the lower end of the sensor element 10 abuts the upper end of the element positioning jig 1191 in FIG. 12A, this abutment is not necessarily required at the time when the workpiece 40β is placed on the sealing assist jig 1192.

When the workpiece 40β is placed on the sealing assist jig 1192 and the sensor element 10 is positioned as described above, temporary sealing (primary compression) is performed, which is the first sealing of the inside of the workpiece 40β, by the compression of the powder compacts 9 (9a, 9b) using the temporary sealing jig 1181. Temporary sealing is a sealing step whose main objective is to temporarily fix the sensor element 10 inside the workpiece 40β. The reason why "temporary" is mentioned here is that the sensor element 10 displaces slightly from a first position in the final sealing (secondary compression) performed thereafter.

The temporary sealing jig 1181 is a cylindrical member with its longitudinal direction coinciding the vertical direction. The temporary sealing jig 1181 is movable up and down vertically by the temporary sealing jig elevating mechanism 1180A not shown in FIGS. 12A and 12B. More specifically, when the temporary sealing jig 1181 is moved vertically downward as indicated by the arrow AR14 while the workpiece 40β is supported from below by the sealing assist jig 1192, the lower end of the temporary sealing jig 1181 abuts a projection portion (flanged portion) 5b provided on the outer periphery of the housing 5 constituting the tubular body 30. In other words, at least the lower end of the temporary sealing jig 1181 and the vicinity thereof have a diameter and a thickness enough to perform such abutment.

The temporary sealing jig 1181 has a cavity 1181a therein that is open upward. With the workpiece 40β placed on the sealing assist jig 1192, the first tip 10a of the sensor element 10 provided with the protective film P projects vertically upward from the end of the tubular body 30. When the temporary sealing jig 1181 abuts the projection portion 5b, however, the first tip 10a is inserted into the cavity 1181a of the temporary sealing jig 1181, so that the sealing assist jig 1192 does not interfere with the sensor element 10. This prevents the protective film P from being damaged or peeled off to be broken.

The temporary sealing jig 1181 is moved down further even after the lower end thereof abuts the projection portion 5b of the housing 5. Then, the tubular body 30 is pressed vertically downward along with the temporary sealing jig 1181 being moved downward, as indicated by the arrow AR15. The annular mounting parts inside the tubular body 30 are supported from below by the sealing assist jig 1192, and thus, begin to keep their positions. Along with the tubular body 30 moving downward, accordingly, the washer 7 is pushed into a relatively inner portion of the tubular body 30. Consequently, the upper end of the sealing assist jig 1192 presses the washer 7, resulting in a state in which a vertically upward force (load) F1 (first force) is applied to the washer 7. If the force F1 is preferably applied to the washer 7, both of the tip of the sealing assist jig 1192 that abuts the washer 7 and the tip of the temporary sealing jig 1181 that abuts the projection portion 5b of the housing 5 do not need to be formed continuously in the radial direction and can be formed non-continuously, for example, can have a slit.

When the force F1 is exerted on the washer 7 from the sealing assist jig 1192, the force F1 is also exerted as a compression force on the powder compacts 9a and 9b through the ceramic supporters 8a and 8b. The powder compacts 9a and 9b are accordingly compressed, and the annular mounting parts are pushed into the tubular body 30 as a whole. Such compression eliminates the gap between the powder compacts 9a and 9b and the sensor element 10, thus bringing the powder compacts 9a and 9b into intimate contact with the sensor element 10. The sensor element 10, which has been displaceable vertically, is fixed by the powder compacts 9a and 9b while being positioned by the element positioning jig 1191. This is the temporary sealing performed in this embodiment. The disposed position of the sensor element 10 in the workpiece 400 after the temporary sealing disposed is referred to as a first position.

Here, the force F1 is applied with magnitude in such a range that does not cause chipping (or cracking) in the sensor element 10 while enabling fixing of the sensor element 10. In other words, in the temporary sealing, the powder compacts 9 are not compressed to such an extent that achieves sufficient airtightness though it is compressed to such an extent that allows the sensor element 10 to be fixed. The airtightness is achieved in a following final sealing step.

In the case where the first position at which the sensor element 10 is positioned is lowered beyond an allowable lower limit position during the temporary sealing, the positioning jig elevating mechanism 1190 is moved up to prevent the first position from being located below the lower limit position.

Figure 12B:
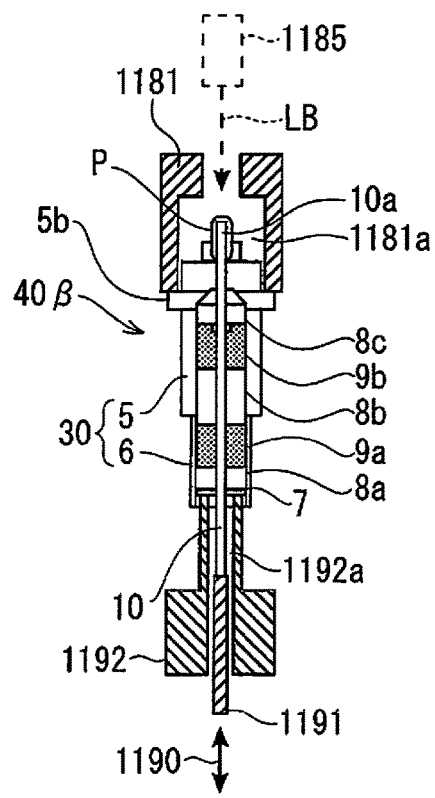

As shown in FIG. 12B, the assembly apparatus 1100 may include a laser displacement meter 1185 to monitor the height level of the sensor element 10 by emitting a laser beam LB toward the first tip 10a of the sensor element 10 exposed in the cavity 1181a from the laser displacement meter 1185. In this case, the positioning jig elevating mechanism 1190 and the element positioning jig 1191 can posture the sensor element 10 based on the monitoring result.

After the temporary sealing completes, the temporary sealing jig 1181 is caused to retract, and with the posture of the workpiece 40β kept by the assembly transport mechanism 1200, the workpiece 40β is delivered to the first inversion jig 1171 and the second inversion jig 1172.

Figure 13:
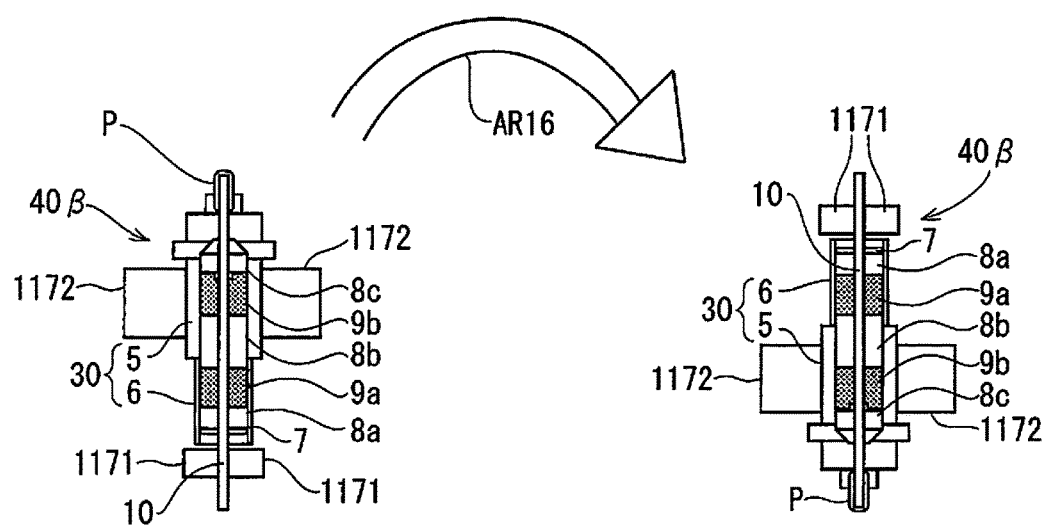
FIG. 13 is a schematic cross-sectional view of the assembly 40 according to the second embodiment during assembly.

The inversion mechanism 1170 vertically inverts the posture of the workpiece 40β after being temporary sealed which has been delivered from the assembly transport mechanism 1200. Specifically, first, the inversion mechanism 1170 drives the first inversion jig 1171 and the second inversion jig 1172 to cause, as shown in FIG. 13, each of the first inversion jig 1171 and the second inversion jig 1172 of the inversion mechanism 1170 to grip the workpiece 40β. The first inversion jig 1171 grips the sensor element 10 projecting vertically downward in the lower part of the workpiece 40β from the lateral side of the sensor element 10, and the second inversion jig 1172 grips the tubular body 30 (more specifically, the housing 5) from the lateral side of the tubular body 30.

The inversion mechanism 1170 then moves the first inversion jig 1171 and the second inversion jig 1172 to cause these jigs to orbit around a predetermined horizontal axis by 180° while keeping the grip states of these jigs such that the portion gripped by the first inversion jig 1171 and the portion gripped by the second inversion jig 1172 are vertically inverted. This vertically inverts the posture of the workpiece 40β as indicated by the arrow AR16. In other words, the workpiece 40β is postured such that the first tip 10a side of the sensor element 10 provided with the protective film P is the lowermost end. In this case, the first inversion jig 1171, the second inversion jig 1172, and the inversion mechanism 1170 function as inversion means for vertically inverting the posture of the workpiece 40β. Specific configurations of the first inversion jig 1171, the second inversion jig 1172, and the inversion mechanism 170 may be any configurations that preferably enable the inversion of the posture of the workpiece 40β.

In this embodiment, the powder compacts 9 are compressed to some extent by the temporary sealing prior to the inversion of the posture, so that the powder compacts 9 are less likely to fall off (drop) due to the inversion than in the first embodiment in which the workpiece 40β is inverted without temporary sealing.

Figure 14A:
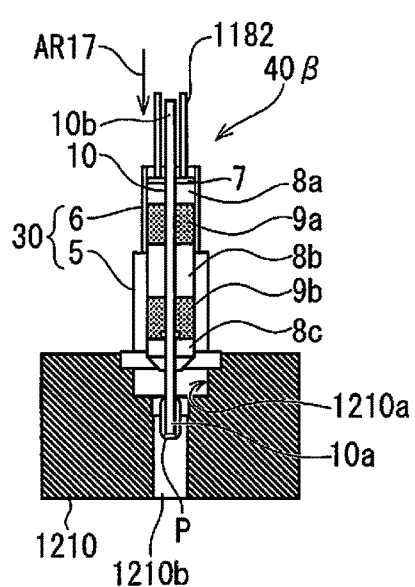
FIGS. 14A and 14B are schematic cross-sectional views of the assembly 40 according to the second embodiment during assembly.

As shown in FIG. 14A, the workpiece 40β whose posture has been inverted is placed on a transport palette 1210 included in the assembly transport mechanism 1200. In the assembly transport mechanism 1200, the transport palette 1210 is movable up and down vertically. The transport palette 1210 is also used to transport, to the assembly wait part 1201, the assembly 40 obtained after all the assembling steps complete.

The transport palette 1210 includes, at the side of its upper surface perpendicular to the vertical direction, a fitting part 1210a that is a recess having a shape corresponding to the housing 5 constituting the assembly 40. Fitting the housing 5 with the fitting part 1210a causes the workpiece 40β to be placed on and fixed to the transport palette 1210 in such a posture that causes its longitudinal direction to extend vertically.

Preferably, when being placed and fixed, the workpiece 40β is positioned so as not to have a rotational deviation in the horizontal plane. This may be achieved by providing anisotropy to the outer peripheral shape of the housing 5 and providing the fitting part 1210a with a shape corresponding to the outer peripheral shape. Alternatively, retaining means (not shown) included in the transport palette 1210 may retain the horizontal posture of the workpiece 40β.

Below the fitting part 1210a, a hole portion 1210b is provided. Although the first tip 10a of the sensor element 10 provided with the protective film P projects vertically downward from the end of the tubular body 30 in the lower part of the workpiece 40β, when the workpiece 40β is placed on the transport palette 1210, the first tip 10a is inserted into the hole portion 1210b, and thus, does not interfere with the transport palette 1210. This prevents the protective film P from being damaged or peeled off to be broken.

When the workpiece 40β is placed on and fixed to the transport palette 1210, subsequently, final sealing (secondary compression) is performed. The final sealing is a sealing step performed to mainly achieve airtightness between the measurement gas space and the reference gas space.

In the final sealing, a final sealing jig elevating mechanism 1180B not shown in FIG. 14A causes the final sealing jig 1182 to move vertically downward from above the workpiece 40β as indicated by the arrow AR17 in FIG. 14A, to cause the lower end of the final sealing jig 1182 to abut the washer 7.

The final sealing jig 1182 is a cylindrical member with its longitudinal direction coinciding the vertical direction, and is movable up and down vertically by the final sealing jig elevating mechanism 1180B. The outside diameter of the final sealing jig 1182 perpendicular to its longitudinal direction is smaller than the outside diameter of each annular mounting part, and the inside diameter of the final sealing jig 1182 is greater than a maximum size of the through hole of each annular mounting part.

Figure 14B:
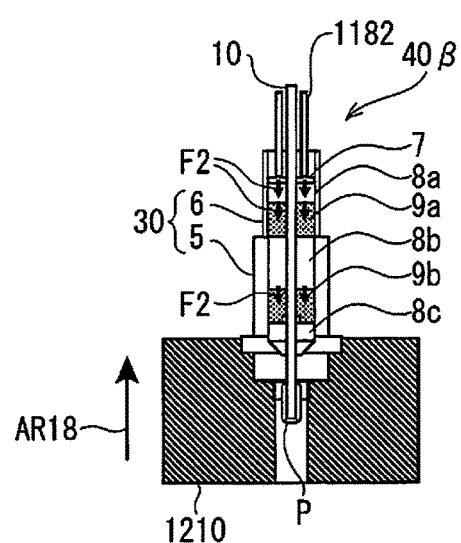

The final sealing jig 1182 abuts the washer 7, causing the assembly transport mechanism 200 to move up the transport palette 1210 vertically as indicated by the arrow AR18 in FIG. 14B.

Then, along with the transport palette 1210 moving upward, the tubular body 30 is pushed vertically upward. On the other hand, the final sealing jig 1182 abuts the washer 7 that is located uppermost among the annular mounting parts inside the tubular body 30, and thus, the annular mounting parts begin to keep their positions. The washer 7 is accordingly pushed into a relatively inner portion of the tubular body 30 along with the transport palette 1210 moving upward. Consequently, the lower end of the final sealing jig 1182 presses the washer 7, resulting in a state in which a vertically downward force (load) F2 (second force) is applied to the washer 7. If the force F2 is preferably applied to the washer 7, the tip of the final sealing jig 1182 that abuts the washer 7 does not need to be formed continuously in the radial direction and can be formed non-continuously, for example, can have a slit.

When the force F2 is exerted on the washer 7 from the final sealing jig 1182, the force F2 is also exerted as a compression force on the powder compacts $9a$ and $9b$ through the ceramic supporters $8a$ and $8b$. In this case, if F2>F1, the powder compacts $9a$ and $9b$ are compressed further, and the annular mounting parts are further pushed into the tubular body 30 as a whole. Consequently, the space between the measurement gas space and the reference gas space is hermetically sealed. This is the final sealing performed in this embodiment.

During the final sealing, the first tip 10a of the sensor element 10 provided with the protective film P is inserted into the hole portion 1210b and does not abut another member. This prevents the protective film P from being damaged or peeled off to be broken during the final sealing.

In the first embodiment, when the assembly 40 is sealed, the protective film P is protected from breakage with the use of the sealing assist jig 111 that has a buffer performance against an impact; according to this embodiment, the first tip 10a of the sensor element 10 provided with the protective film P does not abut another member in the temporary sealing and the final sealing, so that without the use of the sealing assist jig 111, sealing can be achieved in the assembly 40 while protecting the protective film P from breakage.

For reliable hermetic sealing, the force F2 applied to the washer 7 needs to be much greater than the force F1 applied to the washer 7 in the temporary sealing. On the other hand, the final sealing is performed without causing the sensor element 10 to abut another member not only at the first tip 10a side but also at the second tip 10b side. The sensor element 10, which has been fixed by the powder compacts 9a and 9b once in the temporary sealing stage and has been disposed at the first position, thus can be displaced further by even a small amount in the final sealing. On the premise that the disposed position of the sensor element 10 after the final sealing is referred to as a second position, however, if the second position falls within a predetermined error range allowable in terms of characteristics desired for the gas sensor 1, the sensor element 10 can be regarded as being preferably fixed at the second position even upon occurrence of such a displacement.

In the final sealing, thus, the transport palette 1210 is moved up such that the pressure to be applied to the washer 7 by the final sealing jig 1182 has magnitude that causes the second position to fall within a predetermined allowable error range. The upper limit of the pressure can be appropriately determined in view of, for example, material strengths of the final sealing jig 1182 and the washer 7, or the ceramic supporters 8.

Two-stage sealing performed in this embodiment has an effect that a risk of chipping or cracking occurring in the sensor element 10 is reduced compared with the manner of performing sealing only once.

Specifically, in hermitic sealing, a strong force needs to be applied to compress the powder compacts 9, whereas the sensor element 10 needs to be positioned at a predetermined position. Hermitic sealing with the sensor element 10 abutting another member for positioning exerts a strong force also on the portion at which the sensor element 10 abuts the other member, which may cause chipping or cracking occurring in the sensor element 10.

In this embodiment, contrastingly, in the temporary sealing for positioning the sensor element 10, the compression force exerted on the powder compacts 9 is set to be smaller than the force required for hermetic sealing, though the sensor element 10 is caused to abut the element positioning jig 1191. In the final sealing thereafter, the compression force applied to the powder compacts 9 is set large enough to enable hermetic sealing, whereas the sensor element 10 that has been positioned to some extent is prevented from abutting another member. This prevents a strong force to be exerted on the portion at which the sensor element 10 abuts the other member, leading to a lower risk of chipping or cracking occurring in the sensor element 10.

When the final sealing completes, the crimp jig drive mechanism 190 crimps the inner tube 6 as in the first embodiment. Specifically, with the transport palette 1210 and the final sealing jig 1182 remaining disposed also after the final sealing, the crimp jig drive mechanism 190 not shown in FIGS. 15A and 15B runs, thus causing, as indicated by the arrow AR19 in FIG. 15A, the crimp jig 191 to approach the inner tube 6 from the lateral side of the inner tube 6 and crimp the inner tube 6 from its outer peripheral side at the height level immediately above the washer 7. As a result of the final sealing described above, a space is formed inside the inner tube 6 above the washer 7, and thus, the recess 6b is preferably formed at a position immediately above the washer 7 in the inner tube 6, as shown in FIG. 15B. The formation of the recess 6b prevents the annular mounting parts from falling off in the following steps, and as described above, the annular mounting parts are locked inside the tubular body 30. In this case, the crimp jig 191 and the crimp jig drive mechanism 190 function as crimp means for forming the recess 6b that locks the annular mounting parts in the inner tube 6 constituting the tubular body 30. Also in this embodiment, retightening may be performed following the formation of the recess 6b as in the first embodiment.

The formation of the recess 6b described above (or retightening thereafter) completes the assembly 40. After the formation of the recess 6b, the final sealing jig elevating mechanism 1180B not shown in FIGS. 15A and 15B runs again, thus causing the final sealing jig 1182 to move upward as indicated by the arrow AR20 in FIG. 15B and retract to a predetermined retraction position. Also, the assembly transport mechanism 1200 not shown in FIGS. 15A and 15B causes the transport palette 1210 to move vertically downward as indicated by the arrow AR21 in FIG. 15B and return to the position before the final sealing. After that, the assembly transport mechanism 1200 transports the assembly 40 to the assembly wait part 1201.

Consequently, the assembly procedure in the assembly apparatus 1100 completes. When another assembly 40 is subsequently assembled, a similar procedure is repeated from the state shown in FIG. 5A. The resultant assembly 40 is provided to the outside of the assembly apparatus 1100 and is then equipped with the first cover 2, the fixing bolt 3, and the second cover 4. This completes (the main body) of the gas sensor 1.

Also in the procedure for assembling an assembly performed in this embodiment, as in the first embodiment, the annular mounting parts are always annularly mounted to the element dummy or the sensor element. This preferably prevents a problem in which the sensor element cannot be assembled due to the occurrence of a positional deviation.

The first tip of the sensor element having an opening does not pass through the through holes of the annular mounting parts, and thus, even in the use of a sensor element including a protective film at its first tip side, assembling can be performed preferably.

In this embodiment, the first tip of the sensor element provided with the protective film does not abut another member in the temporary sealing and the final sealing. Without the use of a sealing assist jig as used in the first embodiment, thus, sealing can be performed in the assembly while protecting the protective film from breakage.

A strong force is not exerted on the portion at which the sensor element abuts another member in both of the temporary sealing and the final sealing, leading to a lower risk of chipping or cracking occurring in the sensor element than in the case where sealing is performed while the sensor element abuts another member.

As in the assembly procedure described in the first embodiment, the assembly procedure in this embodiment does not necessarily exhibit an operational advantage only when it is used to assemble a sensor element provided with a protective film. That is to say, the assembly procedure in this embodiment can similarly achieve an operational effect irrelevant to a protective film also when a sensor element not provided with a protective film is to be assembled.

Modification of Second Embodiment

In the second embodiment described above, the final sealing is performed by moving up the transport palette 1210, with the final sealing jig 1182 abutting the washer 7. Alternatively, the final sealing may be performed by moving down the final sealing jig 1182 abutting the washer 7 vertically downward, with the transport palette 1210 remaining stationary.

The invention claimed is:

1. A method for assembling a gas sensor, the method comprising the steps of:
   (a) disposing an element dummy with its longitudinal direction coinciding a vertical direction, said element dummy having, a shape similar to a shape of a sensor element including ceramic as a main constituent material and having an elongated shape;
   (b) fitting through holes of annular mounting parts with said element dummy from vertically above, said annular mounting parts each having a disc shape or cylindrical shape, said through holes each having a shape corresponding, to a cross-sectional shape of said sensor element;
   (c) fitting a tubular body with outer peripheries of said annular mounting parts from vertically above;
   (d) abuttingly disposing said sensor element on an upper end of said element dummy such that said element dummy and said sensor element arc arranged in line with each other;
   (e) moving said element dummy vertically downward to move down said sensor element and fitting said through holes of said annular mounting parts with said sensor element, to thereby obtain a workpiece including said sensor element, said annular mounting parts, and said tubular body;
   (f) vertically inverting a posture of said workpiece; and
   (g) pressing said annular mounting parts, wherein:
   in said step b, a plurality of parts including a powder compact of ceramic are fitted with said element dummy as said annular mounting parts, and
   in said step (g), with a tip of said sensor element, located as a lowermost end of said workpiece after said step (f), being in contact with a sealing assist jig, said part located at an uppermost position among said annular mourning parts is pressed vertically downward to compress said powder compact, to thereby seal an inside of said tubular body, said sealing assist jig having a buffer performance against an impact exerted from vertically above.

2. The method according to claim 1, wherein
   said sensor element has a surface of one end on which a protective film is formed,
   in said step (d), said sensor element is disposed such that an end of said sensor element at a side at which said protective film is not formed is supported by said element dummy, and
   in said step (g), with said protective film being in contact with said sealing assist jig, said part located at said uppermost position is pressed vertically downward.

3. The method according to claim 2, wherein said sealing assist jig includes, at its vertical upper end, a buffer member having a buffer performance against an impact exerted from vertically above.

4. The method according to claim 2, wherein said sealing assist jig includes, in its vertical midway portion, an elastic member having a buffer performance against an impact exerted from vertically above.

5. The method according to claim 1, wherein said sealing assist jig includes a buffer member having a buffer performance against an impact exerted from vertically above.

6. The method according to claim 5, wherein said buffer member has a Rockwell hardness of 1 or more and 200 or less and a thickness of 0.1 mm or more and 1.0 mm or less.

7. The method according to claim 1, wherein said sealing assist jig includes, in its vertical midway portion, an elastic member having a buffer performance against an impact exerted from vertically above.

8. The method according to claim 1, further comprising the step of
   (h) after said step (g), crimping an upper end of said tubular body at a position immediately above said part located at an uppermost position among said annular mounting parts from an outer peripheral side of said tubular body to form a recess that locks said annular mounting parts.

9. The method according to claim 8, wherein in said step (h), a cavity formed immediately above said part located at the uppermost position inside said tubular body in said step (g) is crimped.

10. A method for assembling a gas sensor, the method comprising the steps of:
   (a) disposing an element dummy with its longitudinal direction coinciding a vertical direction, said element dummy having a shape similar to a shape of a sensor element including ceramic as a main constituent material and having an elongated shape;
   (b) fitting through holes of annular mounting parts with said element dummy from vertically above, said annular mounting parts each having a disc shape or cylindrical shape, said through holes each having a shape corresponding to a cross-sectional shape of said sensor element;
   (c) fitting a tubular body with outer peripheries of said annular mounting parts from vertically above;
   (d) abuttingly disposing said sensor element on an upper end of said element dummy such that said element dummy and said sensor element are arranged in line with each other;
   (e) moving said element dummy vertically downward to move down said sensor element and fitting said through holes of said annular mounting parts with said sensor element, to thereby obtain a workpiece including said sensor element, said annular mounting parts, and said tubular body;
   (f) vertically inverting a posture of said workpiece; and
   (g) pressing, said annular mounting parts, wherein:
   in said step b, a plurality of parts including a powder compact of ceramic are fitted with said element dummy as said annular mounting parts, and
   said step (g) includes
      (g-1) a step of compressing, said powder compact of said workpiece being in a first posture, and
      (g-2) a step of compressing said powder compact of said workpiece being in a second posture,
      said first posture being a posture of said workpiece before being vertically inverted in said step (f),
      said second posture being a posture of said workpiece after being vertically inverted in said step (f), and
      letting an upper end and a lower end of said sensor element when said workpiece is in said first posture be respectively a first tip and a second tip, in said step (g-1), with said sensor element being positioned from below said second tip using a predetermined positioning jig, a first force is applied to said annular mounting parts vertically upward to compress said powder compact, in said step (f), said workpiece in which said powder compact has been compressed in said step (g-1) is vertically inverted, and in said step (g-2) with said workpiece vertically inverted in said step (f) being supported from below and simultaneously said first tip of said sensor element located at a lowermost end of said workpiece being prevented from abutting another member, a second force greater than said first force applied to said annular mounting parts vertically downward to further compress said powder compact, to thereby seal an inside of said tubular body.

11. The method according to claim 10, wherein
said sensor element has a surface of one end on which a protective film is formed, and
in said step (d), said sensor element is disposed such that an end of said sensor element at a side at which said protective film is not formed is supported by said element dummy.

12. The method according to claim 10, wherein in said step (g-1), with said sensor element being positioned from below using the positioning jig and simultaneously said annular mounting parts being supported from below using a predetermined support jig, said workpiece is depressed from above using a predetermined depressing jig to cause said predetermined support jig to press said part located at a lowermost position among said mounting parts vertically upward, to thereby apply said first force to said annular mounting parts vertically upward.

13. The method according to claim 10, wherein in said step (g-2), said part located at an uppermost position among said annular mounting parts is pressed vertically downward to apply said second force to said annular mounting parts vertically downward.

14. The method according to claim 13, wherein in said step (g-2), with a predetermined abutment member being caused to abut said part located at the uppermost position among said annular mounting parts from vertically above, said workpiece is moved vertically upward to apply said second force to said annular mounting parts vertically downward.

15. The method according to claim 10, further comprising the step of:
(h) after said step (g), crimping an upper end of said tubular body at a position immediately above said part located at an uppermost position among said annular mounting parts from an outer peripheral side of said tubular body to form a recess that locks said annular mounting parts.

16. The method according to claim 15, wherein in said step (h), a cavity formed immediately above said part located at the uppermost position inside said tubular body in said step (g) is crimped.

17. A gas sensor assembly apparatus, comprising:
an element dummy having a shape similar to a shape of a sensor element including ceramic as a main constituent material and having an elongated shape;
a dummy disposing element that disposes said element dummy with its longitudinal direction coinciding a vertical direction;
an annular mounting parts fitting element that fits through holes of annular mounting parts with said element dummy from vertically above, said annular mounting parts each having a disc shape or cylindrical shape, said through holes each having a shape corresponding to a cross-sectional shape of said sensor element;
a tubular body fitting element that fits a tubular body with outer peripheries of said annular mounting parts from vertically above;
an element disposing element that abuttingly disposes said sensor element on an upper end of said element dummy such that said element dummy and said sensor element are arranged in line with each other;
an element fitting element that moves down said element dummy vertically downward to move down said sensor element and fits said through holes of said annular mounting parts with said sensor element, to thereby obtain a workpiece, including said sensor element, said annular mounting parts, and said tubular body;
an inversion element that vertically inverts a posture of said workpiece;
a pressing element that presses said annular mounting parts; and
a sealing assist jig having a buffer performance against an impact exerted from vertically above, wherein
said annular mounting parts comprise a plurality of parts including a powder compact of ceramic,
said inversion element causes a tip of said sensor element that is located as a lowermost end of said workpiece after the posture is vertically inverted to come into contact with said sealing assist jig, and
with said tip of said sensor element being in contact with said sealing assist jig, said pressing element presses said part located at an uppermost position among said annular mounting parts vertically below to compress said powder compact, to thereby seal an inside of said tubular body.

18. The gas sensor assembly apparatus according to claim 17, wherein
said sensor element has a surface of one end on which a protective film is formed,
said element disposing element disposes said sensor element such that an end of said sensor element at a side at which said protective film is not formed is supported by said element dummy, and
with said protective film being in contact with said sealing assist jig, said pressing element presses said part located at said uppermost position vertically downward.

19. The gas sensor assembly apparatus according to claim 18, wherein said sealing assist jig includes, in its vertical upper end, a buffer member having a buffer performance against an impact exerted from vertically above.

20. The gas sensor assembly apparatus according to claim 18, where said sealing assist jig includes, in its vertical midway portion, an elastic member having a buffer performance against an impact exerted from vertically above.

21. The gas sensor assembly apparatus according to claim 17, wherein said sealing assist jig includes, at its vertical upper end, a buffer member having a buffer performance against an impact exerted from vertically above.

22. The gas sensor assembly apparatus according to claim 21, wherein said buffer member has a Rockwell hardness of 1 or more and 200 or less and a thickness of 0.1 mm or more and 1.0 mm or less.

23. The gas sensor assembly apparatus according to claim 17, wherein said scaling assist jig includes, in its vertical midway portion, an elastic member having a buffer performance against an impact exerted from vertically above.

24. The gas sensor assembly apparatus according to claim 17, further comprising
a crimp element that crimps an upper end of said tubular body at a position immediately above said part located at an uppermost position among said annular mounting parts from an outer periphery of said tubular body to form a recess that locks said annular mounting parts.

25. The gas sensor assembly apparatus according to claim 24, wherein said crimp element crimps a cavity formed immediately above said part located at the uppermost position inside said tubular body by said press element.

26. A gas sensor assembly apparatus comprising:
an element dummy having a shape similar to a shape of a sensor element including ceramic as a main constituent material and having an elongated shape;
a dummy disposing element that disposes said element dummy with its longitudinal direction coinciding a vertical direction;
an annular mounting parts fitting element that fits through holes of annular mounting parts with said element dummy from vertically above, said annular mounting parts each having a disc shape or cylindrical shape, said through holes each having a shape corresponding to a cross-sectional shape of said sensor element;
a tubular body fitting element that fits a tubular body with outer peripheries of said annular mounting parts from vertically above;
an element disposing element that abuttingly disposes said sensor element on an upper end of said element dummy such that said element dummy and said sensor element are arranged in line with each other;
an element fitting element that moves down said element dummy vertically downward to move down said sensor element and fits said through holes of said annular mounting parts with said sensor element, to thereby obtain a workpiece including said sensor element, said annular mounting parts, and said tubular body;
an inversion element that vertically inverts a posture of said workpiece; and
a pressing element that presses said annular mounting parts, wherein;
said annular mounting parts comprise a plurality of parts including a powder compact of ceramic,
said pressing element includes
a primary compression element that compresses said powder compact of said workpiece being in a first posture, and
a secondary compression element that compresses said powder compact of said workpiece being in a second posture,
said first posture being a posture of said workpiece that is not vertically inverted by said inversion element,
said second posture being a posture of said workpiece that is vertically inverted by said inversion element, and
letting an upper end and a lower end of said sensor element when said workpiece is in said first posture be respectively a first tip and a second tip,
said primary compression element includes a positioning jig that positions said sensor element from below said second tip, said primary compression element applying a first force to said annular mounting parts vertically upward to compress said powder compact, with said sensor element being positioned by said positioning jig,
said inversion element vertically inverts said workpiece in which said powder compact is compressed by said primary compression element, and
while supporting, from below, said workpiece vertically inverted by said inversion element and simultaneously preventing said first tip of said sensor element located at a lowermost end of said workpiece from abutting another member, said secondary compression element applies a second force greater than said first force to said annular mounting parts to further compress said powder compact, to thereby seal an inside of said tubular body.

27. The gas sensor assembly apparatus according to claim 26, wherein
said sensor element has a surface of one end on which a protective film is formed, and
said element disposing element disposes said sensor element such that an end of said sensor element at a side at which said protective film is not formed is supported by said element dummy.

28. The gas sensor assembly apparatus according to claim 26, wherein
said primary compression element further includes
a support jig that supports said annular mounting parts from below, and
a depressing jig that depresses said workpiece from above, and
while positioning said sensor element from below using said positioning jig and simultaneously supporting said annular mounting parts from below using said support jig, said primary compression element depresses said workpiece from above using said depressing jig to press said part located at a lowermost position among said annular mounting parts vertically upward using said support jig, to thereby apply said first force to said annular mounting parts vertically upward.

29. The gas sensor assembly apparatus according to claim 26, wherein said secondary compression element presses said part located at an uppermost position among said annular mounting parts vertically downward to apply said second force to said annular mounting parts vertically downward.

30. The gas sensor assembly apparatus according to claim 29, wherein
said secondary compression element further includes an abutment member that is caused to abut said part located at the uppermost position among said annular mounting parts from vertically above, and
while causing said abutment member to abut said part, said secondary compression element moves said workpiece vertically upward to apply said second force to said annular mounting parts vertically downward.

31. The gas sensor assembly apparatus according to claim 26, further comprising:
a crimp element that crimps an upper end of said tubular body at a position immediately above said part located at an uppermost position among said annular mounting parts from an outer periphery of said tubular body to form a recess that locks said annular mounting parts.

32. The gas sensor assembly apparatus according to claim 31, wherein said crimp element crimps a cavity formed immediately above said part located at the uppermost position inside said tubular body by said press element.

* * * * *